US011746342B2

(12) United States Patent
Fukada et al.

(10) Patent No.: US 11,746,342 B2
(45) Date of Patent: *Sep. 5, 2023

(54) METHOD FOR MANUFACTURING PROTEIN

(71) Applicant: AJINOMOTO CO., INC., Tokyo (JP)

(72) Inventors: Hiroaki Fukada, Kanagawa (JP);
Hiroka Koguchi, Kanagawa (JP);
Mitsunori Tokura, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 535 days.

This patent is subject to a terminal disclaimer.

(21) Appl. No.: 16/840,945

(22) Filed: Apr. 6, 2020

(65) Prior Publication Data

US 2020/0255869 A1 Aug. 13, 2020

Related U.S. Application Data

(63) Continuation of application No. PCT/JP2018/037542, filed on Oct. 9, 2018.

(30) Foreign Application Priority Data

Oct. 10, 2017 (JP) ................................ 2017-196538

(51) Int. Cl.
| | |
|---|---|
| *C12N 9/48* | (2006.01) |
| *C12P 21/04* | (2006.01) |
| *C12N 9/58* | (2006.01) |
| *C12P 1/02* | (2006.01) |
| *C12P 21/02* | (2006.01) |
| *C12N 15/09* | (2006.01) |
| *C07K 14/37* | (2006.01) |

(52) U.S. Cl.
CPC ............... *C12N 9/58* (2013.01); *C12N 15/09* (2013.01); *C12P 1/02* (2013.01); *C12P 21/02* (2013.01); *C12Y 304/21048* (2013.01); *C07K 14/37* (2013.01); *C12N 2330/50* (2013.01)

(58) Field of Classification Search
CPC .................................... C12N 9/58; C12P 21/02
See application file for complete search history.

(56) References Cited

U.S. PATENT DOCUMENTS

| 6,103,515 A | 8/2000 | Treichler et al. |
| 6,291,209 B1 | 9/2001 | Lehmbeck |
| 11,384,379 B2 | 7/2022 | Yahagi et al. |
| 2014/0370546 A1 | 12/2014 | Landowski et al. |
| 2016/0237466 A1 | 8/2016 | Landowski et al. |

FOREIGN PATENT DOCUMENTS

| EP | 3690040 A1 | 8/2020 |
| JP | 2-104279 A | 4/1990 |
| JP | 2000-507106 A | 6/2000 |
| JP | 2001-017180 A | 1/2001 |
| JP | 2006-512891 A | 4/2006 |
| JP | 2015-512611 A | 4/2015 |
| JP | 2016-131533 A | 7/2016 |
| JP | 2016-523552 A | 8/2016 |
| JP | 2016-158599 A | 9/2016 |
| WO | WO03/089614 A2 | 10/2003 |
| WO | WO2015/093467 A1 | 6/2015 |
| WO | WO-2021251383 A1 * | 12/2021 |

OTHER PUBLICATIONS

Studer. Residue mutations and their impact on protein structure and function: detecting beneficial and pathogenic changes. Biochem. J. (2013) 449, 581-594.*
English Translation of WO 2021/251383. Retrieved on Nov. 22, 2022.*
Inoue, H., et al., "Construction of a starch-inducible homologous expression system to produce cellulolytic enzymes from Acremonium cellulolyticus," J. Ind. Microbiol. Biotechnol. 2013;40:823-830.
International Search Report for PCT Patent App. No. PCT/JP2018/037542 (dated Dec. 25, 2018).
Extended European Search Report for European Patent App. No. 18866436.1 (dated Jun. 29, 2021).
International Preliminary Report on Patentability for PCT Patent App. No. PCT/JP2018/037542 (dated Apr. 23, 2020).

* cited by examiner

*Primary Examiner* — Yong D Pak
(74) *Attorney, Agent, or Firm* — Cermak Nakajima & McGowan LLP; Shelly Guest Cermak

(57) ABSTRACT

A method for producing a protein is provided. An objective protein is produced by culturing *Talaromyces cellulolyticus* having an objective protein-producing ability, which has been modified so that the activity of a YscB protein is reduced, in a culture medium.

15 Claims, 6 Drawing Sheets

Specification includes a Sequence Listing.

[Fig. 1]
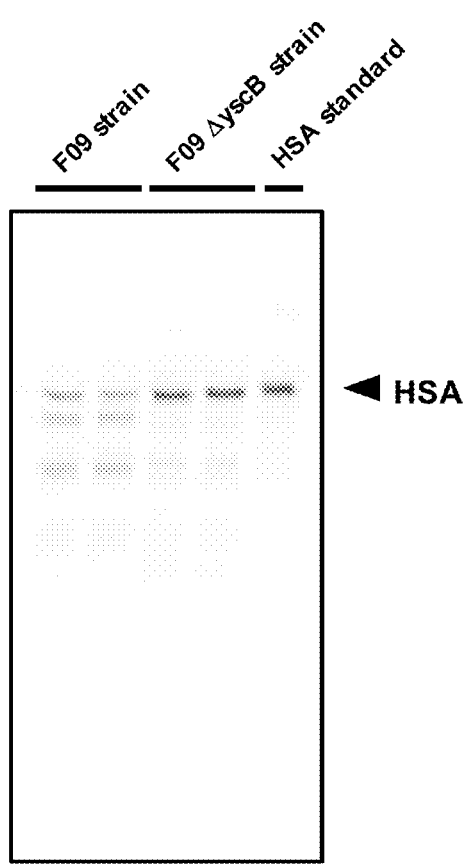

[Fig. 2]
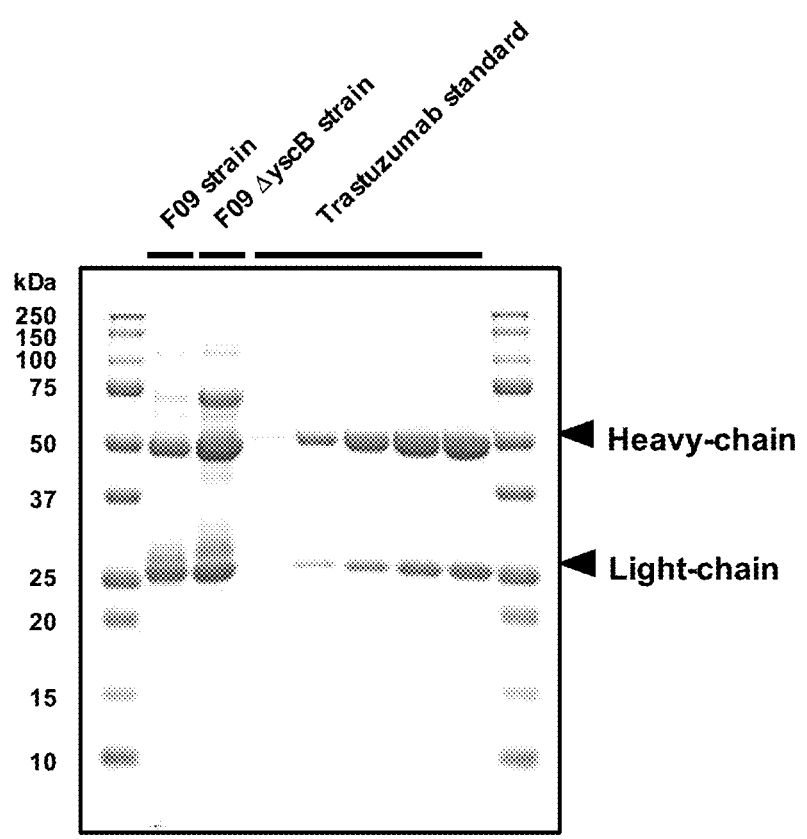

[Fig. 3]
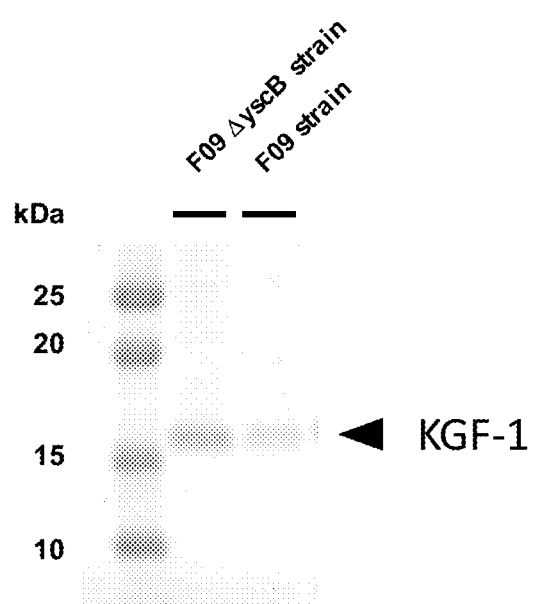

[Fig. 4]
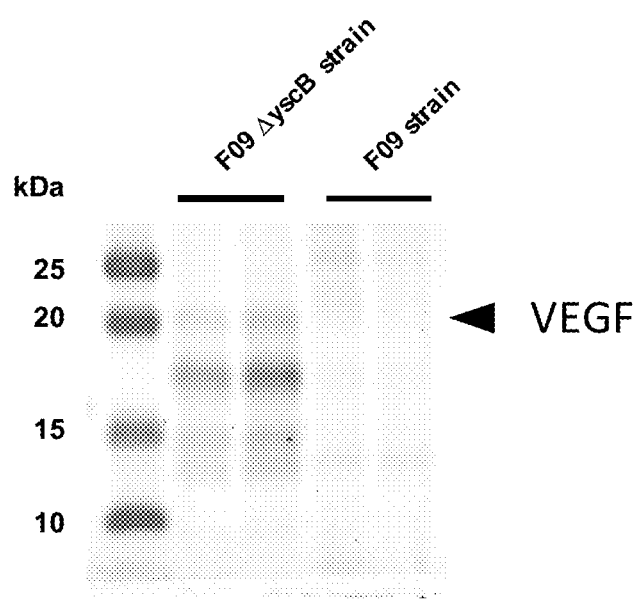

[Fig. 5]
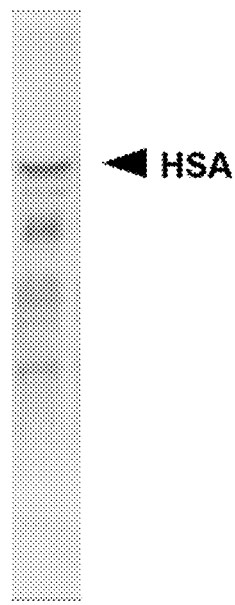

[Fig. 6]
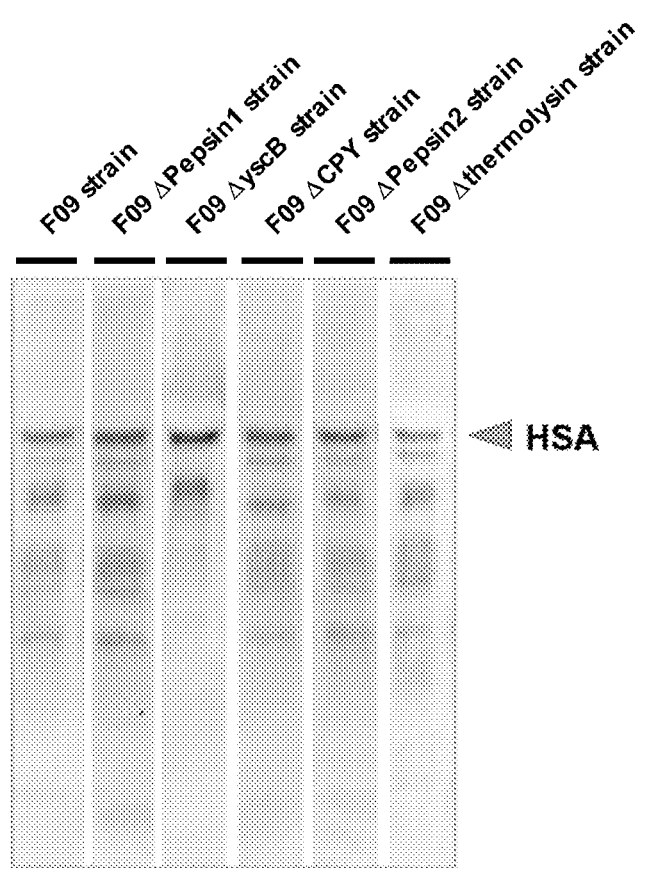

METHOD FOR MANUFACTURING PROTEIN

This application is a continuation of, and claims priority under 35 U.S.C. § 120 to, International Application No. PCT/JP2018/037542, filed Oct. 9, 2018, and claims priority therethrough under 35 U.S.C. § 119 to Japanese Patent Application No. 2017-196538, filed Oct. 10, 2017, the entireties of which are incorporated by reference herein. Also, the Sequence Listing filed electronically herewith is hereby incorporated by reference (File name: 2020-04-06T_US-610_Seq_List; File size: 50 KB; Date recorded: Apr. 6, 2020).

BACKGROUND

Technical Field

The present invention relates to a method for producing a protein.

Background Art

As methods for producing proteins, methods of using various microorganisms such as coryneform bacteria, *Bacillus* bacteria, yeasts, and filamentous fungi have been reported.

For example, Inoue H. et al. (Construction of a starch-inducible homologous expression system to produce cellulolytic enzymes from *Acremonium cellulolyticus*. J Ind Microbiol Biotechnol. 2013 August; 40(8):823-30) discloses production of host-derived cellulases using a filamentous fungus *Talaromyces cellulolyticus* (formerly, *Acremonium cellulolyticus*). In addition, Japanese Patent Laid-open (Translation of PCT Application) No. 2006-512891 discloses production of antibodies using filamentous fungi. In addition, Japanese Patent Laid-open (Kokai) No. 2016-158599 discloses production of multimeric proteins having a cavity using filamentous fungi such as *Talaromyces cellulolyticus*.

In addition, Japanese Patent Laid-open (Translation of PCT Application) No. 2015-512611 and Japanese Patent Laid-open (Translation of PCT Application) No. 2016-523552 disclose production of heterologous proteins using filamentous fungi having an attenuated activity of endogenous protease. In addition, Japanese Patent Laid-open (Translation of PCT Application) No. 2000-507106 discloses production of heterologous proteins using filamentous fungi having an attenuated activity of endogenous alkaline protease.

In addition, Japanese Patent Laid-open (Kokai) No. 1990-104279 discloses production of heterologous proteins using yeast deficient in the activity of carboxypeptidase yscα. This document further describes that the yeast may be further deficient in the activity of a peptidase(s) such as yscA, yscB, yscY, and yscS.

However, no relation between a YscB protein and protein production in *Talaromyces cellulolyticus* has been known.

SUMMARY

It is an aspect to provide a method for producing a protein.

It has been found that the ability of *Talaromyces cellulolyticus* to produce a protein is improved by modifying *Talaromyces cellulolyticus* so that the activity of a YscB protein is reduced.

It is an aspect of the present invention to provide a method for producing an objective protein, comprising culturing *Talaromyces cellulolyticus* having an objective protein-producing ability in a culture medium, wherein the *Talaromyces cellulolyticus* has been modified so that the activity of a YscB protein is reduced as compared with a non-modified strain.

It is an aspect of the present invention to provide the method as described above, wherein the activity of the YscB protein is reduced by reducing the expression of a yscB gene or disrupting a yscB gene.

It is an aspect of the present invention to provide the method as described above, wherein the activity of the YscB protein is reduced by deletion of a yscB gene.

It is an aspect of the present invention to provide the method as described above, wherein the YscB protein is selected from the group consisting of: (a) a protein comprising the amino acid sequence of SEQ ID NO: 43; (b) a protein comprising the amino acid sequence of SEQ ID NO: 43, but which includes substitution, deletion, insertion, and/or addition of 1 to 10 amino acid residues, and wherein said protein has a protease activity; and (c) a protein comprising an amino acid sequence having an identity of 90% or higher to the amino acid sequence of SEQ ID NO: 43, and wherein said protein has a protease activity.

It is an aspect of the present invention to provide the method as described above, wherein the *Talaromyces cellulolyticus* has been modified so that the activity of a CreA protein is reduced as compared with a non-modified *Talaromyces cellulolyticus*.

It is an aspect of the present invention to provide the method as described above, wherein the activity of the CreA protein is reduced by reducing the expression of a creA gene or disrupting a creA gene.

It is an aspect of the present invention to provide the method as described above, wherein the activity of the CreA protein is reduced by deletion of a creA gene.

It is an aspect of the present invention to provide the method as described above, wherein the *Talaromyces cellulolyticus* is derived from *Talaromyces cellulolyticus* strain S6-25 (NITE BP-01685).

It is an aspect of the present invention to provide the method as described above, further comprising collecting the objective protein.

It is an aspect of the present invention to provide the method as described above, wherein the objective protein is accumulated in the culture medium by the culturing.

It is an aspect of the present invention to provide the method as described above, wherein the objective protein is expressed as a fused protein with a signal peptide that functions in *Talaromyces cellulolyticus*.

It is an aspect of the present invention to provide the method as described above, wherein the objective protein is a heterologous protein.

It is an aspect of the present invention to provide the method as described above, wherein the objective protein is a protein derived from human.

It is an aspect of the present invention to provide the method as described above, wherein the objective protein is human serum albumin.

It is an aspect of the present invention to provide the method as described above, wherein the objective protein is an antibody-related molecule.

It is an aspect of the present invention to provide the method as described above, wherein the objective protein is a growth factor.

BRIEF DESCRIPTION OF DRAWINGS

FIG. 1 shows a diagram (photograph) showing a result of production of human serum albumin (HSA) by *T. cellulolyticus* strains F09 and F09ΔyscB.

FIG. 2 shows a diagram (photograph) showing a result of production of Trastuzumab by *T. cellulolyticus* strains F09 and F09ΔyscB.

FIG. 3 shows a diagram (photograph) showing a result of production of Keratinocyte growth factor 1 (KGF-1) by *T. cellulolyticus* strains F09 and F09ΔyscB.

FIG. 4 shows a diagram (photograph) showing a result of production of Vascular endothelial growth factor (VEGF) by *T. cellulolyticus* strains F09 and F09ΔyscB.

FIG. 5 shows a diagram (photograph) showing a result of evaluating protease activity in a supernatant of *T. cellulolyticus* strain F09.

FIG. 6 shows a diagram (photograph) showing a result of evaluating protease activity in a supernatant of *T. cellulolyticus* strain F09 and protease-deficient strains thereof.

DETAILED DESCRIPTION

The method as described herein is a method for producing an objective protein using *Talaromyces cellulolyticus*. *Talaromyces cellulolyticus* used in this method is also referred to as "the microorganism".

<1> Microorganism

The microorganism as described herein is *Talaromyces cellulolyticus* having an objective protein-producing ability, which has been modified so that the activity of a YscB protein is reduced. In the descriptions concerning the microorganism, the microorganism or *Talaromyces cellulolyticus* to be used for constructing the same is also referred to as a "host".

<1-1> *Talaromyces cellulolyticus*

The microorganism can be *Talaromyces cellulolyticus*. A former name of *Talaromyces cellulolyticus* is *Acremonium cellulolyticus*. That is, *Acremonium cellulolyticus* was reclassified as *Talaromyces cellulolyticus* due to revision of phylogenetic taxonomy (FEMS Microbiol. Lett., 2014, 351: 32-41). Specific examples of *Talaromyces cellulolyticus* include strains C1 (Japanese Patent Laid-open (Kokai) No. 2003-135052), CF-2612 (Japanese Patent Laid-open (Kokai) No. 2008-271927), TN (FERM BP-685), S6-25 (NITE BP-01685), Y-94 (FERM BP-5826, CBS 136886), and derivative strains thereof. The phrase "*Talaromyces cellulolyticus*" collectively refers to fungi classified as *Talaromyces cellulolyticus* at any time before, on, and after the filing of the present application. That is, a fungus once classified to *Talaromyces cellulolyticus* should be regarded as *Talaromyces cellulolyticus* even if phylogenetic taxonomy thereof is changed in future.

The strain S6-25 was originally deposited at the independent administrative agency, National Institute of Technology and Evaluation, Patent Microorganisms Depositary (#122, 2-5-8 Kazusakamatari, Kisarazu-shi, Chiba-ken, 292-0818, Japan) on Aug. 8, 2013, and then converted to an international deposit under the provisions of the Budapest Treaty on Nov. 15, 2013, and assigned an accession number of NITE BP-01685. This strain can be obtained from the strain TN (FERM BP-685) and has a high cellulase-producing ability. The strain Y-94 was originally deposited at the National Institute of Bioscience and Human Technology, Agency of Industrial Science and Technology, Ministry of International Trade and Industry (currently, independent administrative agency, National Institute of Technology and Evaluation, International Patent Organism Depositary, #120, 2-5-8 Kazusakamatari, Kisarazu-shi, Chiba-ken, 292-0818, Japan) on Jan. 12, 1983, and then converted to an international deposit under the provisions of the Budapest Treaty on Feb. 19, 1997, and assigned an accession number of FERM BP-5826.

These strains can be obtained from, for example, the depositories at which the strains were deposited.

The microorganism can be obtained by modifying *Talaromyces cellulolyticus* such as the strains exemplified above. That is, the microorganism may be a modified strain derived from any of the strains exemplified above. The microorganism may specifically be, for example, a modified strain derived from the strain S6-25 or Y-94. The microorganism may more specifically be, for example, a modified strain derived from the strain S6-25. The order in which various modifications for constructing the microorganism is not particularly limited.

<1-2> Objective Protein-Producing Ability

The microorganism has an objective protein-producing ability. The phrase "a microorganism having an objective protein-producing ability" refers to a microorganism having an ability to produce an objective protein. The phrase "a microorganism having an objective protein-producing ability" may specifically refer to a microorganism having an ability to express an objective protein and accumulate an objective protein in a culture broth to such a degree that the objective protein can be collected therefrom, when the microorganism is cultured in a culture medium. The phrase "accumulation in a culture broth" may specifically refer to, for example, accumulation in a culture medium, on a cell surface layer, in microbial cells, or in/on a combination thereof. When the objective protein is accumulated outside microbial cells, for example, in a culture medium or on a cell surface layer, is also referred to as "secretion" or "secretory production" of the objective protein. That is, the microorganism may have a secretory production ability of the objective protein, such as an ability to produce the objective protein by secretory production. The objective protein may be accumulated particularly in a culture medium. The accumulation amount of the objective protein may be, for example, 10 μg/L or more, 1 mg/L or more, 100 mg/L or more, or 1 g/L or more, in terms of the accumulation amount in a culture broth. The microorganism may have an ability to produce a single kind of objective protein, or two or more kinds of objective proteins.

The microorganism may be a microorganism inherently having an objective protein-producing ability, or may be a microorganism modified so as to have an objective protein-producing ability. The microorganism can typically be a microorganism inherently having a cellulase-producing ability, that is, an ability to produce cellulase. The microorganism may also be a microorganism modified so that an inherent objective protein-producing ability of the microorganism has been enhanced. The microorganism having an objective protein-producing ability can be obtained by, for example, imparting an objective protein-producing ability to such *Talaromyces cellulolyticus* as mentioned above, or enhancing an objective protein-producing ability of such *Talaromyces cellulolyticus* as mentioned above. The objective protein-producing ability can be imparted or enhanced by, for example, introduction of a genetic construct for expression of the objective protein, introduction of another modification for improving the objective protein-producing ability, or both.

The microorganism has an objective protein-producing ability at least on the basis of possession of a genetic construct for expression of the objective protein. The microorganism may have an objective protein-producing ability specifically on the basis of possession of a genetic construct for expression of the objective protein or on the basis of a combination of possession of a genetic construct for expression of the objective protein and another characteristic. That is, the microorganism has a genetic construct for expression of the objective protein. The microorganism may have one copy or two or more copies of the genetic construct for expression of the objective protein. The microorganism may have a single kind of genetic construct for expression of the objective protein, or may have two or more kinds of genetic constructs for expression of the objective protein. The copy number and the number of kinds of the genetic construct for expression of the objective protein may be read as, respectively, the copy number and the number of kinds of the objective protein.

In the microorganism, the genetic construct for expression of the objective protein may be present on a vector autonomously replicable out of the chromosome such as a plasmid, or may have been introduced into the chromosome. That is, the microorganism may have the genetic construct for expression of the objective protein on a vector, and in other words, may have a vector containing the genetic construct for expression of the objective protein. Also, the microorganism may have the genetic construct for expression of the objective protein on the chromosome. When the microorganism has two or more genetic constructs for expression of the objective protein, it is sufficient that those genetic constructs are possessed by the microorganism so that the objective protein can be produced. For example, all of those genetic constructs may be carried on a single expression vector, or may be carried on the chromosome. Alternatively, those genetic constructs may be separately carried on a plurality of expression vectors, or may be separately carried on a single or a plurality of expression vectors and the chromosome.

The microorganism may be a microorganism inherently having a genetic construct for expression of the objective protein, or may be a microorganism modified so as to have a genetic construct for expression of the objective protein. The microorganism can typically be a microorganism inherently having a genetic construct for expression of cellulase. The microorganism may also be a microorganism introduced with a genetic construct for expression of the objective protein, in addition to or instead of a genetic construct for expression of the objective protein inherently possessed by the microorganism. The microorganism having a genetic construct for expression of the objective protein can be obtained by introducing the genetic construct for expression of the objective protein into such *Talaromyces cellulolyticus* as mentioned above.

The phrase "a genetic construct for expression of an objective protein" refers to a gene expression system configured to be able to express an objective protein. The genetic construct for expression of the objective protein is also referred to as an "expression system for an objective protein" or an "expression unit for an objective protein". The genetic construct for expression of the objective protein includes, in the direction from 5' to 3', a promoter sequence and a nucleotide sequence encoding the objective protein. A promoter sequence is also referred to simply as a "promoter". A nucleotide sequence encoding an amino acid sequence is also referred to as a "gene". For example, A nucleotide sequence encoding the objective protein is also referred to as a "gene encoding an objective protein" or an "objective protein gene". It is sufficient that the objective protein gene is ligated downstream from the promoter so that the objective protein is expressed under the control of the promoter. The genetic construct for expression of the objective protein may also include a regulatory sequence effective for expression of the objective protein, such as an operator and a terminator, at an appropriate position so that it can function. The phrases "expression of an objective protein gene", "expression of an objective protein", "generation of an objective protein", and "production of an objective protein" can be used synonymously with each other, unless otherwise stated. The genetic construct for expression of the objective protein can be appropriately designed according to various conditions such as the type of objective protein.

The promoter is not particularly limited so long as it functions in *Talaromyces cellulolyticus*. The phrase "a promoter that functions in *Talaromyces cellulolyticus*" refers to a promoter having a promoter activity, i.e. a gene transcription activity, in *Talaromyces cellulolyticus*.

The promoter may be a promoter derived from the host, or may be a heterologous promoter. The promoter may be the native promoter of the objective protein gene, or may be a promoter of another gene. The promoter may be an inducible promoter or may be a constitutive promoter. Examples of the promoter include promoters of cellulase genes of microorganisms. Specific examples of the promoter include promoters of cellulase genes of *Talaromyces cellulolyticus*. Examples of the cellulase genes include a cbhI gene (also referred to as cbh1 gene) and a cbhII gene (also referred to as cbh2 gene). That is, examples of the promoter include a promoter of the cbhI gene and a promoter of the cbhII gene. The promoter of the cbhI gene is also referred to as a "cbhI promoter" or a "cbh1 promoter". The promoter of the cbhII gene is also referred to as a "cbhII promoter" or a "cbh2 promoter". The nucleotide sequences of the cbhI and cbhII promoters of *Talaromyces cellulolyticus* are shown in SEQ ID NOS: 41 and 33, respectively. That is, the promoter may be, for example, a promoter having any of the nucleotide sequences of the promoters exemplified above, e.g. the nucleotide sequence of SEQ ID NO: 41 or 33. The promoter may also be, for example, a conservative variant of any of the promoters exemplified above, e.g. a conservative variant of the promoter having the nucleotide sequence of SEQ ID NO: 41 or 33. That is, for example, each of the promoters exemplified above can be used as it is, or after being modified as required. The phrases "cbhI promoter" and "cbhII promoter" include not only the cbhI and cbhII promoters exemplified above, but also include conservative variants thereof. The descriptions concerning conservative variants of the yscB gene below can be similarly applied to conservative variants of the promoter. For example, the promoter may be a DNA having a nucleotide sequence having a homology of 80% or higher, 90% or higher, 95% or higher, 97% or higher, 99% or higher, to the nucleotide sequence of SEQ ID NO: 41 or 33, so long as the original function is maintained. The term "original function" used for the promoter refers to a function of expressing, e.g. inducibly or constitutively expressing, a gene ligated immediately downstream of the promoter. The function of the promoter can be confirmed by, for example, confirming an expression of a gene. The expression of a gene can be confirmed by, for example, using a reporter gene.

The objective protein is not particularly limited. The objective protein may be a protein derived from the host, or may be a heterologous protein. The phrase "heterologous protein" refers to an exogenous protein relative to *Talaromyces cellulolyticus* that produces the protein. The objective protein may be, for example, a protein derived from a microorganism, a protein derived from a plant, a protein derived from an animal, a protein derived from a virus, or a protein of which the amino acid sequence is artificially designed. The objective protein may particularly be a derived from human. The objective protein may be a monomeric protein or a multimeric protein. The term "multimeric protein" refers to a protein that includes two or more subunits, that is, a multimer. In the multimer, the subunits may be linked by covalent bonds such as disulfide bonds, linked by non-covalent bonds such as hydrogen bonds and hydrophobic interaction, or both. The multimer can include one or more intermolecular disulfide bonds. The multimer may be a homo-multimer having a single kind of subunit, or may be a hetero-multimer having two or more kinds of subunits. The phrase "an objective protein is a heterologous protein" may mean that, in cases where the objective protein is a hetero-multimer, at least one subunit is a heterologous protein. That is, all the subunits may be heterologous, or only some of the subunits may be heterologous. The objective protein may be a secretory protein or a non-secretory protein. Although the objective protein may be a secretory protein in nature, or may be a non-secretory protein in nature, it is preferred that the objective protein is a secretory protein in nature. The phrase "protein" also includes substances called peptide, such as oligopeptides and polypeptides.

Examples of the objective protein include, for example, enzymes, physiologically active proteins, receptor proteins, antigenic proteins to be used as vaccines, and any other proteins.

Examples of the enzymes include, for example, cellulase, transglutaminase, protein glutaminase, isomaltodextranase, protease, endopeptidase, exopeptidase, aminopeptidase, carboxypeptidase, collagenase, chitinase, and so forth.

The phrase "cellulase" collectively refers to enzymes catalyzing a reaction of hydrolyzing a glycoside bond contained in cellulose. Examples of cellulase include endo-type cellulase (endoglucanase; EC 3.2.1.4), exo-type cellulase (cellobiohydrolase; EC 3.2.1.91), and cellobiase (beta-glucosidase; EC 3.2.1.21). Cellulase is also referred to as Avicelase, filter paper cellulase (FPase), carboxymethylcellulase (CMCase), or the like depending on the substrate used for activity measurement. Examples of cellulase include, for example, cellulases of fungi such as *Trichoderma reesei* and *Talaromyces cellulolyticus* and cellulases of bacteria such as *Clostridium thermocellum*.

Examples of transglutaminase include, for example, secretory-type transglutaminases of Actinomycetes such as *Streptoverticillium mobaraense* IFO 13819 (WO01/23591), *Streptoverticillium cinnamoneum* IFO 12852, *Streptoverticillium griseocarneum* IFO 12776, and *Streptomyces lydicus* (WO96/06931), and of filamentous fungi such as *Oomycetes* (WO96/22366). Examples of protein glutaminase include, for example, protein glutaminase of *Chryseobacterium proteolyticum* (WO2005/103278). Examples of isomaltodextranase include, for example, isomaltodextranase of *Arthrobacter globiformis* (WO2005/103278).

Examples of the physiologically active proteins include, for example, growth factors, hormones, cytokines, and antibody-related molecules.

Specific examples of the growth factors include, for example, epidermal growth factor (EGF), insulin-like growth factor-1 (IGF-1), transforming growth factor (TGF), nerve growth factor (NGF), brain-derived neurotrophic factor (BDNF), Vascular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), acidic fibroblast growth factor (aFGF or FGF1), basic fibroblast growth factor (bFGF or FGF2), keratinocyte growth factor (KGF-1 or FGF7, and, KGF-2 or FGF10), and hepatocyte growth factor (HGF).

Specific examples of the hormones include, for example, insulin, glucagon, somatostatin, human growth hormone (hGH), parathyroid hormone (PTH), calcitonin, and exenatide.

Specific examples of the cytokines include, for example, interleukins, interferons, and tumor necrosis factors (TNFs).

The growth factors, hormones, and cytokines may not be strictly distinguished from one another. For example, a physiologically active protein may be only one of growth factors, hormones, and cytokines, or may be more than one of these.

Furthermore, a physiologically active protein may be an intact protein, or may be a part of a protein. Examples of a part of a protein include, for example, a part having physiological activity. Specific examples of a part having physiological activity include, for example, teriparatide, a physiologically active peptide consisting of the N-terminal 34 amino acid residues of parathyroid hormone (PTH).

The phrase "antibody-related molecule" refers to a protein having a single domain or a combination of two or more domains such as the domains constituting a complete antibody. Examples of the domains constituting a complete antibody include heavy chain domains VH, CH1, CH2, and CH3, and light chain domains VL and CL. The antibody-related molecule may be a monomeric protein, or may be a multimeric protein, so long as it contains the above-mentioned molecular species. When the antibody-related molecule is a multimeric protein, it may be a homo-multimer having a single kind of subunit, or may be a hetero-multimer having two or more kinds of subunits. Specific examples of the antibody-related molecules include, for example, complete antibody, Fab, F(ab'), F(ab')$_2$, Fc, dimer having a heavy chain (H chain) and a light chain (L chain), Fc-fusion protein, heavy chain (H chain), light chain (L chain), light chain Fv (scFv), sc(Fv)$_2$, disulfide-bonded Fv (sdFv), diabody, and VHH fragment (Nanobody (registered trademark)). More specific examples of the antibody-related molecules include, for example, trastuzumab and nivolumab.

The receptor proteins are not particularly limited. A receptor protein may be, for example, a receptor protein for any of physiologically active proteins and other physiologically active substances. Examples of the other physiologically active substances include, for example, neurotransmitters such as dopamine. Furthermore, a receptor protein may be an orphan receptor of which the corresponding ligand is not known.

The antigen proteins to be used as vaccines are not particularly limited, so long as they are proteins that can induce an immune response. An antigen protein can be appropriately selected depending on the intended object of the immune response.

In addition, examples of other proteins include liver-type fatty acid-binding protein (LFABP), fluorescent protein, immunoglobulin-binding protein, albumin, and extracellular protein. Examples of the fluorescent protein include green fluorescent protein (GFP). Examples of the immunoglobulin-binding protein include protein A, protein G, and protein L. Examples of albumin include human serum albumin.

Examples of the extracellular protein include fibronectin, vitronectin, collagen, osteopontin, laminin, and partial sequences thereof. Laminin is a protein having a heterotrimeric structure having an α chain, a β chain, and a γ chain. Examples of laminin include laminin of mammals.

Examples of the mammals include primates such as human, monkey, and chimpanzee; rodents such as mouse, rat, hamster, and guinea pig; and other various mammals such as rabbit, horse, cattle, sheep, goat, pig, dog, and cat. Particular examples of the mammals include human. Examples of the subunit chains of laminin, such as α, β, and γ chains; include 5 kinds of α chains, for example, α1 to α5, 3 kinds of β chains, for example, β1 to β3, and 3 kinds of γ chains, for example, γ1 to γ3. Laminin is made up of various isoforms depending on combinations of these subunits. Specific examples of laminin include, for example, laminin 111, laminin 121, laminin 211, laminin 213, laminin 221, laminin 311, laminin 321, laminin 332, laminin 411, laminin 421, laminin 423, laminin 511, laminin 521, and laminin 523. Examples of the partial sequence of laminin include laminin E8, which is an E8 fragment of laminin. Laminin E8 is a protein having a heterotrimeric structure consisting of an E8 fragment of α chain (α chain E8), an E8 fragment of β chain (β chain E8), and an E8 fragment of γ chain (γ chain E8). The subunit chains of laminin E8 (i.e. α chain E8, (3 chain E8, and γ chain E8) are also collectively referred to as "E8 subunit chains". Examples of the E8 subunit chains include E8 fragments of the laminin subunit chains exemplified above. Laminin E8 is made up of various isoforms depending on combinations of these E8 subunit chains. Specific examples of laminin E8 include, for example, laminin 111E8, laminin 121E8, laminin 211E8, laminin 221E8, laminin 332E8, laminin 421E8, laminin 411E8, laminin 511E8, and laminin 521E8.

The objective protein gene can be used as it is, or after being modified as required. The objective protein gene can be modified, for example, to obtain a desired activity. The descriptions concerning conservative variants of the yscB gene and the YscB protein below can be similarly applied to variants of the objective protein gene and the objective protein. For example, the objective protein gene may be modified so that the amino acid sequence of the encoded objective protein includes substitution, deletion, insertion, and/or addition of one or several amino acid residues. A protein specified with the type of organism from which the protein is derived is not limited to proteins per se found in that organism, and shall also include proteins having any of the amino acid sequences of proteins found in that organism and variants thereof. That is, for example, the term "protein derived from human" is not limited to proteins per se found in human, and shall also include proteins having any of the amino acid sequences of proteins found in human and variants thereof. Furthermore, in the objective protein gene, any codon(s) may be replaced with respective equivalent codon(s) thereof. For example, the objective protein gene may be modified so that it has optimal codons according to codon frequencies in the chosen host.

The objective protein may have another amino acid sequence in addition to such an amino acid sequence of the objective protein as exemplified above. That is, the objective protein may be a fusion protein with another amino acid sequence. The "another amino acid sequence" is not particularly limited, so long as an objective protein having a desired characteristic can be obtained. The "another amino acid sequence" can be appropriately selected depending on various conditions such as use purpose thereof. Examples of the "another amino acid sequence" include, for example, a signal peptide, also referred to as "signal sequence", a peptide tag, and a recognition sequence of a protease. The "another amino acid sequence" may be bound to, for example, either one or both of the N-terminus and C-terminus of the objective protein. As the "another amino acid sequence", one kind of amino acid sequence may be used, or two or more kinds of amino acid sequences may be used in combination.

The signal peptide can be used for, for example, secretory production of the objective protein. The signal peptide may be bound to the N-terminus of the objective protein. That is, in one embodiment, the construct includes, in the direction from 5' to 3', a promoter sequence, a nucleotide sequence encoding the signal peptide, and a nucleotide sequence encoding the objective protein. In this case, it is sufficient that the nucleotide sequence encoding the objective protein is ligated downstream from the nucleotide sequence encoding the signal peptide so that the objective protein is expressed as a fusion protein with the signal peptide. In such a fusion protein, the signal peptide and the objective protein may be or may not be adjacent to each other. That is, the phrase "an objective protein is expressed as a fusion protein with a signal peptide" includes not only when an objective protein is expressed as a fusion protein with a signal peptide in which the signal peptide and the objective protein are adjacent to each other, but also includes when an objective protein is expressed as a fusion protein in which the signal peptide and the objective protein are fused with each other via another amino acid sequence. When producing an objective protein by secretory production using a signal peptide, typically, the signal peptide may be cleaved at the time of secretion, and the objective protein not having the signal peptide may be secreted outside microbial cells. That is, the phrase "an objective protein is expressed as a fusion protein with a signal peptide" or the phrase "an objective protein includes a signal peptide" means that it is sufficient that the objective protein is made up of a fusion protein with a signal peptide at the time of expression, and it does not necessarily mean that the eventually-obtained objective protein is made up of a fusion protein with a signal peptide.

The signal peptide is not particularly limited so long as it functions in *Talaromyces cellulolyticus*. The phrase "a signal peptide that functions in *Talaromyces cellulolyticus*" refers to a signal peptide providing secretion of the objective protein when the signal peptide is ligated to the N-terminus of the objective protein.

The signal peptide may be a signal peptide derived from the host, or may be a heterologous signal peptide. The signal peptide may be the native signal peptide of the objective protein, or may be a signal peptide of another protein. Examples of the signal peptide include signal peptides of secretory cellulases of microorganisms. Specific examples of the signal peptide include signal peptides of secretory cellulases of *Talaromyces cellulolyticus*. Examples of the secretory cellulases include a CbhI protein encoded by a cbhI gene, also referred to as Cbh1 protein, and a CbhI protein encoded by a cbhII gene, also referred to as Cbh2 protein. That is, examples of the signal peptide include a signal peptide of the CbhI protein and a signal peptide of the CbhII protein. The signal peptide of the CbhI protein is also referred to as a "CbhI signal peptide" or a "Cbh1 signal peptide". The signal peptide of the CbhII protein is also referred to as a "CbhII signal peptide" or a "Cbh2 signal peptide". The amino acid sequence of the CbhI signal peptide of *Talaromyces cellulolyticus* is shown in SEQ ID NO: 42. That is, the signal peptide may be, for example, a signal peptide having any of the amino acid sequences of the signal peptides exemplified above, e.g. the amino acid sequence of SEQ ID NO: 42. The signal peptide may also be, for example, a conservative variant of any of the signal peptides exemplified above, e.g. a conservative variant of the signal peptide having the amino acid sequence of SEQ ID NO: 42. That is, for example, each of the signal peptides exemplified above can be used as it is, or after being modified as required. The phrases "CbhI signal peptide" and "CbhII signal peptide" include not only the CbhI and CbhII signal peptides exemplified above, but also include conservative variants thereof. The descriptions concerning conservative variants of the YscB protein below can be similarly applied to conservative variants of the signal peptide. For example, the signal peptide may be a peptide having the amino acid sequence of SEQ ID NO: 42, but which includes substitution, deletion, insertion, and/or addition of one or several amino acid residues at one or several positions, so long as the original function is maintained. The term "one or several" mentioned above in the variant of the signal peptide is, specifically, for example, 1 to 7, 1 to 5, 1 to 3, or 1 to 2. For example, the signal peptide may also be a peptide having an amino acid sequence having a homology of 80% or higher, 90% or higher, 95% or higher, 97% or higher, 99% or higher, to the amino acid sequence of SEQ ID NO: 42, so long as the original function is maintained. The term "original function" used for the signal peptide refers to a function of providing secretion of the objective protein when the signal peptide is ligated to the N-terminus of the objective protein. The function of the signal peptide can be confirmed by, for example, confirming secretion of a protein due to ligation of the signal peptide to the N-terminus of the protein.

Specific examples of the peptide tag include His tag, FLAG tag, GST tag, Myc tag, MBP (maltose binding protein), CBP (cellulose binding protein), TRX (thioredoxin), GFP (green fluorescent protein), HRP (horseradish peroxidase), ALP (alkaline phosphatase), and Fc region of antibody. The peptide tag can be utilized for, for example, detection and purification of the expressed objective protein.

Specific examples of the recognition sequence of a protease include the recognition sequence of the HRV3C protease, the recognition sequence of the Factor Xa protease, and the recognition sequence of the proTEV protease. The recognition sequence of a protease can be used for, for example, cleavage of the expressed objective protein. Specifically, for example, when the objective protein is expressed as a fusion protein with a peptide tag, if a recognition sequence of a protease is introduced into the connection part of the objective protein and the peptide tag, the peptide tag can be cleaved from the expressed objective protein by using a protease to obtain the objective protein not having the peptide tag.

The N-terminal region of the eventually-obtained objective protein may be the same as that of the natural protein, or may not be the same as that of the natural protein. For example, the N-terminal region of the eventually-obtained objective protein may be that of the natural protein including addition or deletion of one or several amino acid residues. Although the number of the "one or several" amino acid residues may differ depending on the full length or structure of the objective protein, specifically, it can be 1 to 20, 1 to 10, 1 to 5, or 1 to 3.

Furthermore, the objective protein may also be expressed as a protein that includes a pro-structure moiety (proprotein). When the objective protein is expressed as a proprotein, the eventually-obtained objective protein may be or may not be the proprotein. That is, the proprotein may be processed into the mature protein by cleavage of the pro-structure moiety. The cleavage can be attained with, for example, a protease. When a protease is used, generally, the proprotein can be cleaved at a position substantially the same as that of the natural protein, or at exactly the same position as that of the natural protein so that the same mature protein as the natural mature protein is obtained, in view of the activity of the eventually-obtained protein. Therefore, generally, a specific protease that cleaves the proprotein at such a position that the same protein as the naturally occurring mature protein is generated is a particular example. However, the N-terminal region of the eventually-obtained objective protein may not be the same as that of the natural protein as described above. For example, depending on type, purpose of use etc. of the objective protein to be produced, a protein having an N-terminus longer or shorter by one to several amino acid residues compared with the natural protein may have more appropriate activity. Proteases usable in the present invention include, for example, commercially available proteases such as Dispase (produced by Boehringer Mannheim) as well as those obtainable from culture broth of a microorganism such as culture broth of actinomycetes. Such proteases may be used in an un-purified state, or may be used after purification to an appropriate purity as required.

The objective protein gene can be obtained by, for example, cloning. For cloning, for example, nucleotides, such as genomic DNA and cDNA, containing the objective protein gene can be used. Furthermore, the objective protein gene can also be obtained by, for example, total synthesis based on the nucleotide sequence thereof (Gene, 60(1), 115-127 (1987)). The obtained objective protein gene can be used as it is, or after being modified as required. That is, a variant of an objective protein gene may be obtained by modifying the objective protein gene. A gene can be modified by a known technique. For example, an objective mutation can be introduced into an objective site of DNA by the site-specific mutation method. Examples of the site-specific mutation method include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of an objective protein gene may be totally synthesized. Furthermore, the obtained objective protein gene can be subject to modification such as introduction of a promoter sequence as required, to thereby obtain the genetic construct for expression of the objective protein. Incidentally, other elements of the genetic construct for expression of the objective protein, such as a promoter sequence, and the genetic construct for expression of the objective protein can be obtained in a similar manner to that for obtaining the objective protein gene.

Genes can be modified by known methods. For example, an objective mutation can be introduced into a target site of DNA by the site-specific mutagenesis method. Examples of the site-specific mutagenesis method include a method of using PCR (Higuchi, R., 61, in PCR Technology, Erlich, H. A. Eds., Stockton Press (1989); Carter P., Meth. In Enzymol., 154, 382 (1987)), and a method of using a phage (Kramer, W. and Frits, H. J., Meth. in Enzymol., 154, 350 (1987); Kunkel, T. A. et al., Meth. in Enzymol., 154, 367 (1987)).

Methods for introducing the genetic construct for expression of the objective protein into *Talaromyces cellulolyticus* are not particularly limited. The phrase "introduction of a genetic construct for expression of an objective protein" refers to making a host harbor the genetic construct, and may specifically refer to introducing an objective protein gene into a host so that the objective protein can be expressed. The phrase "introduction of a genetic construct for expression of an objective protein" includes not only when the genetic construct for expression of the objective protein that has been preliminarily constructed is introduced into a host at once, but also includes when a part of the genetic construct for expression of the objective protein is introduced into a host and the genetic construct for expression of the objective protein is constructed in the host, unless otherwise stated. For example, an objective protein gene may be introduced downstream relative to a promoter inherent to the host to thereby construct the genetic construct for expression of the objective protein on the chromosome of the host.

The genetic construct for expression of the objective protein can be introduced into a host by using, for example, a vector containing the genetic construct for expression of the objective protein. A vector containing the genetic construct for expression of the objective protein is also referred to as an "expression vector of an objective protein". The vector containing the genetic construct for expression of the objective protein can be constructed by, for example, ligating the genetic construct for expression of the objective protein with a vector. Also, for example, when a vector contains a promoter, the vector containing the genetic construct for expression of the objective protein can also be constructed by ligating an objective protein gene downstream the promoter. By introducing an expression vector of the objective protein, a transformant transformed with the vector can be obtained, and that is, the genetic construct for expression of the objective protein can be introduced into the host. The vector is not particularly limited so long as it is autonomously replicable in cells of the host. The vector may be a single copy vector, a low copy vector, or a high copy vector. The vector may contain a marker gene for selection of transformants. The vector may contain a promoter and a terminator for expressing the introduced gene.

Furthermore, the genetic construct for expression of the objective protein may be introduced into the chromosome of a host. Introduction of a gene into the chromosome can be carried out by homologous recombination. Specifically, the genetic construct for expression of the objective protein can be introduced into the chromosome of a host by transforming the host with a recombinant DNA containing the genetic construct to thereby induce homologous recombination between the genetic construct and a target region of the chromosome of the host. The structure of the recombinant DNA to be used for homologous recombination is not particularly limited as long as it causes homologous recombination in a desired manner. For example, a host can be transformed with a linear DNA containing the genetic construct for expression of the objective protein and further containing upstream and downstream sequences of the substitution target region on the chromosome at the respective ends, so that homologous recombination occurs at each of upstream and downstream sides of the target region, to thereby replace the target region with the genetic construct. The recombinant DNA to be used for homologous recombination may contain a marker gene for selection of transformants. Incidentally, introduction of a part of the genetic construct for expression of the objective protein, such as an objective protein gene and a promoter, into the chromosome can be carried out in a similar manner to that for introduction of the entire genetic construct for expression of the objective protein into the chromosome.

The marker gene can be appropriately selected according to the phenotype such as auxotrophy of the host. For example, when the host shows uracil auxotrophy due to mutation in a pyrF or pyrG gene, a strain introduced with a desired modification can be selected by using a pyrF or pyrG gene as a marker gene and using complementation of uracil auxotrophy, i.e. using uracil prototroph, as an indicator. Furthermore, as the marker gene, a drug resistance gene such as hygromycin resistance gene can be used.

Transformation can be carried out by, for example, a method generally used for transformation of eukaryotic microorganisms such fungi and yeasts. Examples of such a method include the protoplast method.

<1-3> Reduction in Activity of YscB Protein

The microorganism has been modified so that the activity of a YscB protein is reduced. The microorganism has been modified so that, specifically, the activity of the YscB protein is reduced as compared with a non-modified strain. The microorganism may have been modified so that, more specifically, for example, the expression of the yscB gene is reduced or the yscB gene is disrupted. By modifying *Talaromyces cellulolyticus* so that the activity of the YscB protein is reduced, the objective protein-producing ability of *Talaromyces cellulolyticus* can be improved, and that is, production of the objective protein by *Talaromyces cellulolyticus* can be increased.

Hereinafter, the YscB protein and the yscB gene encoding the same will be explained.

The YscB protein is a protease. The phrase "protease" refers to a protein having an activity of catalyzing a reaction of hydrolyzing a protein. This activity is also referred to as a "protease activity".

The nucleotide sequence of the yscB gene (including introns) of *Talaromyces cellulolyticus* strain S6-25 is shown as SEQ ID NO: 32, and the amino acid sequence of the YscB protein encoded by this gene is shown as SEQ ID NO: 43. That is, the yscB gene may be, for example, a gene having the nucleotide sequence shown as SEQ ID NO: 32. Also, the YscB protein may be, for example, a protein having the amino acid sequence shown as SEQ ID NO: 43. The expression "a gene or protein has a nucleotide or amino acid sequence" includes when a gene or protein includes the nucleotide or amino acid sequence among other sequences, unless otherwise stated, and when a gene or protein has only the nucleotide or amino acid sequence.

The yscB gene may be a variant of any of the yscB genes exemplified above, such as a gene having the nucleotide sequence shown as SEQ ID NO: 32, so long as the original function thereof is maintained. Similarly, the YscB protein may be a variant of any of the YscB proteins exemplified above, such as a protein having the amino acid sequence shown as SEQ ID NO: 43, so long as the original function thereof is maintained. Such a variant is also referred to as "conservative variant". The term "yscB gene" includes not only the yscB genes exemplified above, but also includes conservative variants thereof. Similarly, the term "YscB protein" includes not only the YscB proteins exemplified above, but also includes conservative variants thereof. Examples of the conservative variants include, for example, homologues and artificially modified versions of the yscB genes and YscB proteins exemplified above.

The expression "the original function is maintained" means that a variant of a gene or protein has a function, such as activity or property, corresponding to the function, such as activity or property, of the original gene or protein. That is, the expression "the original function is maintained" used for the yscB gene means that a variant of the gene encodes a protein that maintains the original function. Furthermore, the expression "the original function is maintained" used for the YscB protein means that a variant of the protein has the protease activity.

The protease activity can be measured by incubating the enzyme with a substrate (a protein), and measuring the enzyme-dependent degradation of the substrate. The protease activity can also be measured by using a commercial kit for measuring the protease activity.

Hereinafter, examples of the conservative variants will be explained.

Homologues of the yscB genes and homologues of the YscB proteins can be easily obtained from public databases by, for example, BLAST search or FASTA search using any of the nucleotide sequences of the yscB genes exemplified above or any of the amino acid sequences of the YscB proteins exemplified above as a query sequence. Furthermore, homologues of the yscB genes can be obtained by, for example, PCR using a chromosome of organisms such as *Talaromyces cellulolyticus* as the template, and oligonucleotides prepared on the basis of any of the nucleotide sequences of these known yscB genes as primers.

The yscB gene may be a gene encoding a protein having any of the amino acid sequences of the YscB proteins exemplified above, such as the amino acid sequence shown as SEQ ID NO: 43, but which includes substitution, deletion, insertion, and/or addition of one or several amino acid residues at one or several positions, so long as the original function thereof is maintained. Although the number meant by the term "one or several" mentioned above may differ depending on the positions of amino acid residues in the three-dimensional structure of the protein or the types of amino acid residues, specifically, it can be, for example, 1 to 50, 1 to 40, 1 to 30, 1 to 20, 1 to 10, 1 to 5, or 1 to 3.

The aforementioned substitution, deletion, insertion, and/or addition of one or several amino acid residues is a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues as mentioned above includes a naturally occurring mutation due to an individual difference, or a difference of species of the organism from which the gene is derived (mutant or variant).

The yscB gene may also be a gene encoding a protein having an amino acid sequence having a homology of, for example, 80% or more, 90% or more, 95% or more, 97% or more, or 99% or more, to the total amino acid sequence of any of the amino acid sequences of the YscB proteins exemplified above, such as the amino acid sequence shown as SEQ ID NO: 43, so long as the original function thereof is maintained. In this description, "homology" means "identity".

The yscB gene may also be DNA that is able to hybridize under stringent conditions with a complementary sequence of any of the nucleotide sequences of the yscB genes exemplified above, such as the nucleotide sequence shown as SEQ ID NO: 32, or with a probe that can be prepared from the complementary sequence, so long as the original function thereof is maintained. The term "stringent conditions" refers to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, not less than 99% homologous, hybridize to each other, and DNAs less homologous than the above do not hybridize to each other, or conditions of washing of typical Southern hybridization, i.e., conditions of washing once, 2 or 3 times, at a salt concentration and temperature corresponding to 1×SSC, 0.1% SDS at 60° C., 0.1×SSC, 0.1% SDS at 60° C., 0.1×SSC, 0.1% SDS at 68° C.

The probe may be, for example, a part of a sequence that is complementary to the gene as described above. Such a probe can be prepared by PCR using oligonucleotides prepared on the basis of the nucleotide sequences of known genes as primers and a DNA fragment containing any of these nucleotide sequences as a template. As the probe, for example, a DNA fragment having a length of about 300 bp can be used. In such a case, the washing conditions of the hybridization may be, for example, 50° C., 2×SSC and 0.1% SDS.

Furthermore, the yscB gene may be a gene in which any codon(s) is/are replaced with respective equivalent codon(s). That is, the yscB gene may be a variant of any of the yscB genes exemplified above due to the degeneracy of the genetic code.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244, Higgins et al. (1989) CABIOS 5:151-153, Corpet et al.

(1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST (BLAST 2.0) can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other. The term "identity" between amino acid sequences may mean an identity calculated by blastp with default scoring parameters (i.e. Matrix, BLOSUM62; Gap Costs, Existence=11, Extension=1; Compositional Adjustments, Conditional compositional score matrix adjustment), unless otherwise stated. The term "identity" between nucleotide sequences may mean an identity calculated by blastn with default scoring parameters (i.e. Match/Mismatch Scores=1, −2; Gap Costs=Linear), unless otherwise stated.

The aforementioned descriptions concerning variants of the genes and proteins can also be similarly applied to any proteins such as the objective protein, and genes encoding them.

<1-4> Other Characteristics

The microorganism may have other desired characteristics, such as modification, so long as the objective protein-producing ability is not spoiled. Examples of the modification include modification for improving the objective protein-producing ability of *Talaromyces cellulolyticus*. Specific examples of the modification include modification of reducing the activity of a CreA protein. These characteristics and modifications can be used solely or in any appropriate combination.

That is, the microorganism may have been modified so that, for example, the activity of a CreA protein is reduced. The microorganism may have been modified so that, specifically, the activity of the CreA protein is reduced as compared with a non-modified strain. The microorganism may have been modified so that, more specifically, for example, the expression of a creA gene is reduced or a creA gene is disrupted. The creA gene is a gene encoding a transcription factor involved in catabolite repression. The creA gene is known to be involved in the expression of cellulase (Mol Gen Genet. 1996 Jun. 24; 251(4):451-60, Biosci Biotechnol Biochem. 1998 December; 62(12):2364-70) in filamentous fungi.

The nucleotide sequence of the creA gene of *Talaromyces cellulolyticus* strain S6-25 is shown as SEQ ID NO: 44. That is, the creA gene may be, for example, a gene having the nucleotide sequence shown as SEQ ID NO: 44. Also, the CreA protein may be, for example, a protein having the amino acid sequence encoded by the nucleotide sequence shown as SEQ ID NO: 44. The creA gene and the CreA protein may be a conservative variant of the creA gene and CreA protein exemplified above, respectively. The descriptions concerning conservative variants of the yscB gene and the YscB protein can be similarly applied to conservative variants of the creA gene and the CreA protein. Incidentally, the expression "the original function is maintained" used for the CreA protein means that a variant of the protein has a function as a transcription factor involved in catabolite repression.

<1-5> Method for Reducing Activity of Protein

Hereinafter, methods for reducing the activity of a protein such as the YscB protein will be described. The methods for reducing the activity of a protein described below can also be utilized for disruption of the wild-type PhoS protein.

The expression "the activity of a protein is reduced" means that the activity of the protein is reduced as compared with a non-modified strain. Specifically, the expression "the activity of a protein is reduced" means that the activity of the protein per cell is reduced as compared with that of a non-modified strain. The term "non-modified strain" used herein refers to a control strain that has not been modified so that the activity of an objective protein is reduced. Examples of the non-modified strain include a wild-type strain and parent strain. Specific examples of the non-modified strain include strains exemplified above in relation to the description of *Talaromyces cellulolyticus*. That is, in an embodiment, the activity of a protein may be reduced as compared with *Talaromyces cellulolyticus* strain S6-25. The state that "the activity of a protein is reduced" also includes a state that the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the gene (i.e. the amount of the protein). The state that "the number of molecules of the protein per cell is reduced" also includes a state that the protein does not exist at all. The state that "the function of each molecule of the protein is reduced" also includes a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" means that the expression of the gene is reduced as compared with a non-modified strain. Specifically, the expression "the expression of a gene is reduced" means that the expression of the gene per cell is reduced as compared with that of a non-modified strain. More specifically, the expression "the expression of a gene is reduced" may mean that the transcription amount of the gene (i.e. the amount of mRNA) is reduced, and/or the translation amount of the gene (i.e. the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene. The term "expression control sequence" collectively refers to sites that affect the expression of a gene, such as a promoter. Expression control sequences can be identified by, for example, using a promoter search vector or gene analysis software such as GENETYX. When an expression control sequence is modified, one or more nucleotides, two or more nucleotides, or three or more nucleotides, of the expression control sequence are modified. The transcription efficiency of a gene can be reduced by, for example, replacing the promoter of the gene on a chromosome with a weaker promoter. The term "weaker promoter" means a promoter providing an attenuated transcription of a gene compared with an inherent wild-type promoter of the gene. Examples of weaker promoters include, for example, inducible promoters. That is, an inducible promoter may function as a weaker promoter under a non-induced condition, such as in the absence of the corresponding inducer. Furthermore, a partial region or the whole region of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" means that a gene is modified so that a protein that can normally function is not produced. The state that "a protein that normally functions is not produced" includes a state that the protein is not produced at all from the gene, and a state that the protein of which the function, such as activity or property, per molecule is reduced or eliminated is produced from the gene.

Disruption of a gene can be attained by, for example, deleting the gene on a chromosome. The term "deletion of a gene" refers to deletion of a partial or entire region of the coding region of the gene. Furthermore, the entire gene including sequences upstream and downstream from the coding region of the gene on a chromosome may be deleted. The sequences upstream and downstream from the coding region of the gene may include, for example, an expression control sequence of the gene. The region to be deleted may be any region such as an N-terminal region, that is, a region encoding an N-terminal region of a protein, an internal region, or a C-terminal region, that is, a region encoding a C-terminal region of a protein, so long as the activity of the protein can be reduced. Deletion of a longer region can usually more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, it is preferred that reading frames of the sequences upstream and downstream from the region to be deleted are not the same. Inconsistency of reading frames may cause a frameshift downstream of the region to be deleted. In the case of the creA gene, specifically, for example, this gene can be disrupted by deleting a region corresponding to positions 3262 to 4509 of SEQ ID NO: 44.

Disruption of a gene can also be attained by, for example, introducing a mutation for an amino acid substitution (missense mutation), a stop codon (nonsense mutation), addition or deletion of one or two nucleotide residues (frame shift mutation), or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another nucleotide sequence into a coding region of the gene on a chromosome. Site of the insertion may be in any region of the gene, and insertion of a longer nucleotide sequence can usually more surely inactivate the gene. It is preferred that reading frames of the sequences upstream and downstream from the insertion site are not the same. Inconsistency of reading frames may cause a frameshift downstream of the region to be deleted. The other nucleotide sequence is not particularly limited so long as a sequence that reduces or eliminates the activity of the encoded protein is chosen, and examples thereof include, for example, marker genes and genes useful for production of the objective protein.

Particularly, disruption of a gene may be carried out so that the amino acid sequence of the encoded protein is deleted. In other words, the modification for reducing the activity of a protein can be attained by, for example, deleting the amino acid sequence, such as a partial or entire region of the amino acid sequence, of the protein, specifically, modifying a gene so as to encode a protein of which the amino acid sequence, such as a partial or entire region of the amino acid sequence, is deleted. The term "deletion of the amino acid sequence of a protein" refers to deletion of a partial or entire region of the amino acid sequence of the protein. In addition, the term "deletion of the amino acid sequence of a protein" means that the original amino acid sequence disappears in the protein, and also includes cases where the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or entire region of the coding region of a gene, a region encoded by the deleted region can be deleted in the encoded protein. In addition, for example, by introduction of a stop codon into the coding region of a gene, a region encoded by the downstream region of the introduction site can be deleted in the encoded protein. In addition, for example, by frameshift in the coding region of a gene, a region encoded by the frameshift region can be deleted in the encoded protein. The aforementioned descriptions concerning the position and length of the region to be deleted in deletion of a gene can be similarly applied to the position and length of the region to be deleted in deletion of the amino acid sequence of a protein.

Such modification of a gene on a chromosome as described above can be attained by, for example, preparing a disruption-type gene modified so that it is unable to produce a protein that normally functions, and transforming a host with a recombinant DNA containing the disruption-type gene to cause homologous recombination between the disruption-type gene and the wild-type gene on a chromosome and thereby substitute the disruption-type gene for the wild-type gene on the chromosome. In this procedure, if a marker gene selected according to the characteristics of the host such as auxotrophy is included in the recombinant DNA, the operation becomes easier. Examples of the disruption-type gene include a gene of which a partial or entire region of the coding region is deleted, gene including a missense mutation, gene including a nonsense mutation, gene including a frame shift mutation, and gene inserted with an insertion sequence such as a transposon or marker gene. The protein encoded by the disruption-type gene has a conformation different from that of the wild-type protein, even if it is produced, and thus the function thereof is reduced or eliminated.

The structure of the recombinant DNA to be used for homologous recombination is not particularly limited as long as it causes homologous recombination in a desired manner. For example, a host can be transformed with a linear DNA containing any chosen sequence and further containing upstream and downstream sequences of the substitution target region on the chromosome at the respective ends, so that homologous recombination occurs at each of upstream and downstream sides of the substitution target region, to thereby replace the substitution target region with the chosen sequence in one step. As such a chosen sequence, for example, a sequence containing a marker gene can be used.

The marker gene can be appropriately selected according to the phenotype such as auxotrophy of the host. For example, when the host shows uracil auxotrophy due to mutation in a pyrF or pyrG gene, a strain introduced with a desired modification can be selected by using a pyrF or pyrG gene as marker gene and using complementation of uracil auxotrophy, i.e. using uracil prototroph, as an indicator. Also, for example, when the host shows methionine auxotrophy due to mutation in a sC gene (sulfate permease gene), a strain introduced with a desired modification can be selected by using a sC gene as a marker gene and using complementation of methionine auxotrophy, i.e. using methionine prototroph, as an indicator. Furthermore, as the marker gene, a drug resistance gene such as hygromycin resistance gene can be used.

Modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

A reduction in the activity of a protein can be confirmed by measuring the activity of the protein. The activity of the YscB protein can be measured, for example, as described above. The activity of the CreA protein can be measured by, for example, measuring the degree of catabolite repression. The degree of catabolite repression can be measured by, for example, measuring cellulase production under culture conditions containing glucose as a carbon source. That is, specifically, a reduction in the activity of the CreA protein can be confirmed, for example, on the basis of, as an indicator, improvement in cellulase production under culture conditions containing glucose as a carbon source.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, and so forth (Molecular cloning (Cold Spring Harbor Laboratory Press, Cold Spring Harbor (USA), 2001)). The amount of mRNA, such as the number of molecules of the mRNA per cell, may be reduced to, for example, 50% or less, 20% or less, 10% or less, 5% or less, or 0% of that of a non-modified strain.

A reduction in the amount of a protein can be confirmed by Western blotting using antibodies (Molecular cloning (Cold Spring Harbor Laboratory Press, Cold Spring Harbor (USA) 2001)). The amount of the protein, such as the number of molecules of the protein per cell, may be reduced to, for example, 50% or less, 20% or less, 10% or less, 5% or less, or 0% of that of a non-modified strain.

Disruption of a gene can be confirmed by determining nucleotide sequence of a part or the whole of the gene, restriction enzyme map, full length, or the like of the gene depending on the means used for the disruption.

Transformation can be carried out by, for example, a method generally used for transformation of eukaryotic microorganisms such fungi and yeasts. Examples of such a method include the protoplast method.

<2> Method

By using the microorganism, the objective protein can be produced. Specifically, by culturing the microorganism, the objective protein can be produced. That is, the method may specifically be a method for producing the objective protein, that includes culturing the microorganism in a culture medium.

The culture medium to be used is not particularly limited, so long as the microorganism can proliferate, and the objective protein is produced. As the culture medium, for example, a liquid culture medium containing a carbon source, nitrogen source, phosphate source, sulfur source, and ingredients such as other various organic and inorganic ingredients as required can be used. The types and concentrations of the culture medium components can be appropriately chosen by those skilled in the art. Regarding specific culture medium compositions, for example, culture medium compositions disclosed in prior reports concerning *Talaromyces cellulolyticus* (Japanese Patent Laid-open (Kokai) No. 2003-135052, Japanese Patent Laid-open (Kokai) No. 2008-271826, Japanese Patent Laid-open (Kokai) No. 2008-271927, etc.) or culture medium compositions used for culturing other various cellulase-producing microorganisms such as *Trichoderma reesei* can be used as a reference.

The carbon source is not particularly limited, so long as the microorganism can utilize it and produce the objective protein. Examples of the carbon source include, for example, saccharides and cellulosic substrates. Specific examples of the saccharides include, for example, glucose, fructose, galactose, xylose, arabinose, sucrose, lactose, cellobiose, blackstrap molasses, hydrolysate of starch, and hydrolysate of biomass. Specific examples of the cellulosic substrates include, for example, microcrystalline cellulose (Avicel), filter paper, waste paper, pulp, wood, rice straw, wheat straw, rice husk, rice bran, wheat bran, sugarcane bagasse, coffee grounds, and tea lees. The cellulosic substrate may also be used after being subject to a pretreatment such as hydrothermal decomposition treatment, acid treatment, alkaline treatment, steaming, blasting, and grinding. Examples of preferred commercially-available cellulosic substrates include Solka-floc (International Fiber Corp, North Tonawanda, N.Y., U.S.A). As the carbon source, one kind of carbon source may be used, or two or more kinds of carbon sources may be used in combination.

Specific examples of the nitrogen source include, for example, ammonium salts such as ammonium sulfate, ammonium chloride, and ammonium phosphate, organic nitrogen sources such as peptone, yeast extract, meat extract, corn steep liquor, and soybean protein decomposition product, ammonia, and urea. As the nitrogen source, one kind of nitrogen source may be used, or two or more kinds of nitrogen sources may be used in combination.

Specific examples of the phosphate source include, for example, phosphate salts such as potassium dihydrogenphosphate and dipotassium hydrogenphosphate, and phosphoric acid polymers such as pyrophosphoric acid. As the phosphate source, one kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, one kind of sulfur source may be used, or two or more kinds of sulfur sources may be used in combination.

Specific examples of the other various organic and inorganic components include, for example, inorganic salts such as sodium chloride, and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing these such as peptone, casamino acid, yeast extract, and soybean protein decomposition product. As the other various organic and inorganic components, one kind of component may be used, or two or more kinds of components may be used in combination.

Culture conditions are not particularly limited, so long as the microorganism can proliferate, and the objective protein is produced. The culture can be performed with, for example, conditions typically used for the culture of microorganisms such as filamentous fungi. Regarding specific culture conditions, for example, culture conditions disclosed in prior reports concerning *Talaromyces cellulolyticus* (Japanese Patent Laid-open (Kokai) No. 2003-135052, Japanese Patent Laid-open (Kokai) No. 2008-271826, Japanese Patent Laid-open (Kokai) No. 2008-271927, etc.) or culture conditions used for culturing other various cellulase-producing microorganisms such as *Trichoderma reesei* can be used as a reference.

The culture can be performed, for example, under aerobic conditions using a liquid medium. The culture under aerobic conditions can be performed, specifically, as a culture with aeration, shaking, stirring, or a combination thereof. The culture temperature may be, for example, 15 to 43° C., and may particularly be approximately 30° C. The culture period may be, for example, 2 hours to 20 days. The culture can be performed as batch culture, fed-batch culture, continuous culture, or a combination of these. The culture medium used at the start of the culture can also be referred to as "starting medium". The culture medium supplied to the culture system (e.g. fermentation tank) in the fed-batch culture or the continuous culture can also be referred to as "feed medium". To supply a feed medium to the culture system in the fed-batch culture or the continuous culture can also be referred to as "feed". The culture may also be performed separately as a seed culture and a main culture. For example, the seed culture may be performed using a solid medium such as an agar medium, and the main culture may be performed using a liquid medium. The culture may be continued, for example, until the carbon source present in the culture medium is consumed, or until the activity of the microorganism is lost.

The culture medium components each may be present in the starting medium, the feed medium, or both. The types of the components present in the starting medium may be or may not be the same as those of the components present in the feed medium. Furthermore, the concentrations of the components present in the starting medium may be or may not be the same as the concentrations of the components present in the feed medium. Furthermore, two or more kinds of feed media having components of different types and/or different concentrations may be used. For example, when feeding is intermittently performed two or more times, the types and/or concentrations of components contained in the feed medium may be or may not be the same for each feeding.

The concentrations of various components can be measured by gas chromatography (Hashimoto, K. et al. 1996. Biosci. Biotechnol. Biochem. 70:22-30) or HPLC (Lin, J. T. et al. 1998. J. Chromatogr. A. 808: 43-49).

By culturing the microorganism as mentioned above, the objective protein is expressed and a culture broth containing the objective protein is obtained. The objective protein may be accumulated in a culture medium, on a cell surface layer, in microbial cells, or in/on a combination thereof. The objective protein may be accumulated particularly in microbial cells.

Production of the objective protein can be confirmed by known methods used for detection or identification of proteins. Examples of such methods include, for example, SDS-PAGE, Western blotting, mass spectrometry, N-terminal amino acid sequence analysis, and enzyme activity measurement. One of these methods may be used alone, or two or more of these methods may be used in combination as required.

The objective protein generated can be collected as required. That is, the method for producing the objective protein may include collecting the objective protein generated. Specifically, the objective protein can be collected as an appropriate fraction containing the objective protein. Examples of such a fraction include, for example, a culture broth, a culture supernatant, microbial cells, and a processed product of microbial cells, such as a disruption product, a lysate, and an extract (cell-free extract). The microbial cells may also be provided, for example, in a form of immobilized cells immobilized on a carrier such as acrylamide and carrageenan.

Furthermore, the objective protein may be separated and purified to a desired extent. The objective protein may be provided in a form of a free enzyme, or may be provided in a form of an immobilized enzyme immobilized on a solid phase such as a resin.

When the objective protein is accumulated in the culture medium, for example, solids such as microbial cells can be removed from the culture broth by centrifugation or the like, and then the objective protein can be separated and purified from the culture supernatant.

When the objective protein is accumulated in microbial cells, for example, the microbial cells can be subject to a treatment such as disruption, lysis, or extraction, and then the objective protein can be separated and purified from the treated product. The microbial cells can be collected from the culture broth by centrifugation or the like. The treatment such as disruption, lysis, or extraction can be performed by known methods. Examples of such methods include, for example, disruption by ultrasonication, disruption in Dyno-Mill, disruption in bead mill, disruption with French press, and lysozyme treatment. One of these methods may be used alone, or two or more of these methods may be used in combination as required.

When the objective protein is accumulated on a cell surface layer, for example, the objective protein can be solubilized and then separated and purified from the solubilized product. Solubilization can be performed by known methods. Examples of such methods include, for example, an increase in a salt concentration and use of a surfactant. One of these methods may be used alone, or two or more of these methods may be used in combination as required.

Purification of the objective protein, such as purification of the objective protein from such a supernatant, treated product, or solubilized product as described above, can be performed by known methods used for purification of proteins. Examples of such methods include, for example, ammonium sulfate fractionation, ion exchange chromatography, hydrophobic chromatography, affinity chromatography, gel filtration chromatography, and isoelectric precipitation. One of these methods may be used alone, or two or more of these methods may be used in combination as required.

In the culture broth, enzyme(s) other than the objective protein, including cellulases, and hemicellulases such as xylanase, xylobiase (beta-xylosidase), and arabinofuranosidase, may also be produced and accumulated together with the objective protein. The objective protein may be collected as a mixture with such other enzyme(s), or may be collected separately from such other enzyme(s).

The objective protein collected may be made into a formulation as required. The dosage form of the formulation is not particularly limited, and can be appropriately chosen according to various conditions such as use purpose of the objective protein. Examples of the dosage form include, for example, solution, suspension, powder, tablet, pill, and capsule. For preparing such a formulation, for example, pharmaceutically acceptable additives such as excipients, binders, disintegrating agents, lubricants, stabilizers, corrigents, odor-masking agents, perfumes, diluents, and surfactants can be used.

EXAMPLES

Hereinafter, the present invention will be more specifically explained with reference to non-limiting examples.

(1) Construction of *T. Cellulolyticus* yscB Gene-Deletion Strain F09ΔyscB

The strain F09ΔyscB was constructed from the *Talaromyces cellulolyticus* strain F09 (Japanese Patent Laid-open (Kokai) No. 2016-131533) as a parent strain by disruption of the yscB gene (SEQ ID NO: 32) according to the following procedure. The strain F09 is a strain having a mutation (single nucleotide substitution) in a pyrF gene obtained from the *T. cellulolyticus* strain S6-25 (NITE BP-01685) as a parent strain. The strain F09 shows uracil auxotrophy due to the mutation in the pyrF gene. First, a DNA fragment for yscB gene disruption having a nucleotide sequence consisting of an upstream region of the yscB gene of *T. cellulolyticus*, a hygromycin-resistant gene, and a downstream region of the yscB gene of *T. cellulolyticus* ligated in this order was prepared according to the following procedure. PCR was performed by using the genomic DNA of the *T. cellulolyticus* strain Y-94 (FERM BP-5826) as the template in combination with primers of SEQ ID NOS: 1 and 2, to amplify the upstream region of the yscB gene, or in combination with primers of SEQ ID NOS: 3 and 4, to amplify the downstream region of the yscB gene. Separately, PCR was performed by using pcDNA3.1/Hygro(+) (Life Technologies) containing the hygromycin-resistant gene as the template and primers of SEQ ID NOS: 5 and 6, to amplify the hygromycin-resistant gene (including promoter and terminator). The PCR products were each purified by using Wizard SV Gel and PCR Clean-Up System (Promega). In-Fusion HD Cloning Kit (Takara Bio) was used to incorporate the purified PCR products into a pUC plasmid included in the kit and to thereby ligate them. *E. coli* JM109 was transformed with the reaction product, and cultured on LB agar medium containing 100 mg/L ampicillin at 37° C. overnight, to form colonies. A plasmid pUC-yscB::hyg, into which the DNA fragment for yscB gene disruption has been incorporated, was obtained from an obtained transformant by using Wizard Plus Miniprep System (Promega). PCR was performed by using the plasmid pUC-yscB::hyg as the template and primers of SEQ ID NOS: 1 and 4, to amplify the DNA fragment for yscB gene disruption, and the fragment was concentrated and purified by ethanol precipitation.

Then, the strain F09 was inoculated into a culture medium containing 12 g/L Potato Dextrose Broth (Difco) and 20 g/L Bacto Agar (Difco), and cultured at 30° C. One agar disk excised from around the edge of a colony formed on the agar medium was inoculated into a culture medium containing 24 g/L Potato Dextrose Broth, and gyratory culture (220 rpm) was carried out at 30° C. for 2 days. Cells were collected by centrifugation (5000 rpm for 5 minutes), and added to 30 mL of a solution containing 10 g/L Yatalase (Takara Bio), 10 mM $KH_2PO_4$, and 0.8 M NaCl (pH6.0). Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$), to prepare 1 mL of a protoplast solution. A 200-μL aliquot of the protoplast solution was mixed with 10 μg of the purified DNA fragment for yscB disruption, and 50 μL of Tris-HCl buffer (pH7.5) containing 400 g/L PEG4000 and 10 mM $CaCl_2$), and left on ice for 30 minutes. Then, the mixture was further mixed with 1 mL of Tris-HCl buffer (pH7.5) containing 400 g/L PEG4000 and 10 mM $CaCl_2$), and left at a room temperature for 15 minutes to allow transformation. Protoplasts were collected by centrifugation (2000 rpm for 10 minutes), inoculated into a minimal medium (10 g/L Glucose, 10 mM $NH_4Cl$, 10 mM $KH_2PO_4$, 7 mM KCl, 2 mM $MgSO_4$, 0.06 mg/L $H_3BO_3$, 0.26 mg/L $(NH_4)_6Mo_7O_{24}$-$4H_2O$, 1 mg/L $FeCl_3$-$6H_2O$, 0.4 mg/L $CuSO_4$-$5H_2O$, 0.08 mg/L $MnCl_2$, 2 mg/L $ZnCl_2$, and 20 g/L Bacto Agar) containing 1 M sucrose, 1 g/L uracil, and 1 g/L uridine, cultured at 30° C. for 1 day, then overlaid with a medium containing 0.5 g/L Hygromycin B, 24 g/L Potato Dextrose Broth, and 7 g/L Bacto Agar, and further cultured at 30° C. for 3 days, to select hygromycin-resistant strains. A colony that appeared was inoculated into a minimal medium containing 0.5 g/L Hygromycin B and cultured at 30° C. for 4 days, and then replacement of the yscB gene with the hygromycin-resistant gene was confirmed, to obtain the strain F09ΔyscB, which is a yscB gene-disruption strain derived from F09.

(2) Construction of Strains Expressing Human Serum Albumin (HSA) and Culture Evaluation Strains expressing human serum albumin (HSA) were constructed from the *T. cellulolyticus* strains F09 and F09ΔyscB as parent strains according to the following procedure.

First, a DNA fragment for expressing HSA having a nucleotide sequence consisting of an upstream region of the creA gene of *T. cellulolyticus*, an upstream region of the cbh2 gene (cbh2 promoter; SEQ ID NO: 33) of *T. cellulolyticus*, a coding sequence of cbh1 secretion signal (SEQ ID NO: 34), a HSA gene (SEQ ID NO: 35), a downstream region of the cbh2 gene (cbh2 terminator; SEQ ID NO: 36) of *T. cellulolyticus*, a pyrF gene marker (SEQ ID NO: 37) of *T. cellulolyticus*, and a downstream region of the creA gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 7 and 8, to amplify the upstream region of the creA gene, in combination with primers of SEQ ID NOS: 9 and 10, to amplify the upstream region of the cbh2 gene, in combination with primers of SEQ ID NOS: 11 and 12, to amplify the coding sequence of cbh1 secretion signal, in combination with primers of SEQ ID NOS: 13 and 14, to amplify the downstream region of the cbh2 gene, in combination with primers of SEQ ID NOS: 15 and 16, to amplify the downstream region of the pyrF gene marker, or in combination with primers of SEQ ID NOS: 17 and 18, to amplify the downstream region of the creA gene. Separately, PCR was performed by using a totally synthesized gene purchased from Eurofins as the template and primers of SEQ ID NOS: 19 and 20, to amplify the HSA gene. The PCR products were purified by using Wizard SV Gel and PCR Clean-Up System (Promega). The purified PCR products were mutually ligated by repeating PCR using a mixture of each combination of two of the purified PCR products as the template, and incorporated by using In-Fusion HD Cloning Kit (Takara Bio) into a pUC plasmid included in the kit. *E. coli* JM109 was transformed with the reaction product, and cultured on LB agar medium containing 100 mg/L ampicillin at 37° C. overnight, to form colonies. A plasmid pUC-creA::Pcbh2-HSA-pyrF, into which the DNA fragment for expressing HSA has been incorporated, was obtained from an obtained transformant by using Wizard Plus Miniprep System (Promega). PCR was performed by using the plasmid pUC-creA::Pcbh2-HSA-pyrF as the template and primers of SEQ ID NOS: 7 and 18, to amplify the DNA fragment for expressing HSA, and the fragment was concentrated and purified by ethanol precipitation. Incidentally, ligation of the upstream and downstream regions of the creA gene at the respective ends of the HSA expressing sequence enables insertion of the HSA expressing sequence not into a random site of the genome but into the creA gene region as the target.

Then, the strains F09 and F09ΔyscB were each cultured and converted to protoplasts in a similar manner to Example (1), and transformed with the purified DNA fragment for expressing HSA in a similar manner to Example (1). The protoplasts were collected by centrifugation (2000 rpm for 10 minutes), inoculated into a minimal medium containing 1 M sucrose, and cultured at 30° C. for 7 days, to select strains of which the uracil auxotrophy was complemented. A colony that appeared was inoculated into a minimal medium and cultured at 30° C. for 4 days, and then replacement of the creA gene region with the HSA expressing sequence was confirmed, to obtain HSA expressing strains derived from the strains F09 and F09ΔyscB.

The HSA expressing strains derived from the strains F09 and F09ΔyscB were each inoculated into a culture medium containing 12 g/L Potato Dextrose Broth (Difco) and 20 g/L Bacto Agar (Difco), and cultured at 30° C. One agar disk excised from around the edge of a colony formed on the agar medium was inoculated into 20 mL of a liquid culture medium containing 50 g/L Solka Floc, 24 g/L $KH_2PO_4$, 5 g/L $(NH_4)_2SO_4$, 3 g/L Urea, 1 g/L Tween80, 1.2 g/L $MgSO_4$-$7H_2O$, 0.01 g/L $ZnSO_4$-$7H_2O$, 0.01 g/L $MnSO_4$-$5H_2O$, and 0.01 g/L $CuSO_4$-$5H_2O$, and cultured at 220 rpm at 30° C. for 7 days. The obtained culture broth was filtered with a 0.22 µm filter, to thereby obtain a culture supernatant.

In order to confirm secretory production of HSA, the obtained culture supernatant was subject to SDS-PAGE, followed by Western blotting using an anti-HSA antibody (SIGMA, A6684). Results are shown in FIG. 1. In the case of the strain F09, a band corresponding to HSA was observed but it was extremely weak, and bands presumed to correspond to degradation products were observed at a low-molecular-weight side. By contrast, in the case of the strain F09ΔyscB, an intense band corresponding to HSA was observed, and bands were scarcely observed at a low-molecular-weight side. From these results, it was suggested that HSA was degraded in the case of the strain F09, whereas degradation of HSA was suppressed and thereby the secretory production amount of HSA was increased in the case of the strain F09ΔyscB. Thus, HSA was quantified by ELISA using Albumin ELISA Quantitation Kit, Human (Bethyl Laboratories, inc.). Results are shown in Table 1. It was confirmed that the strain F09ΔyscB provided an increase in the secretory production amount of HSA as compared with the strain F09, and hence, it was shown that the secretory production amount of HSA is improved by deletion of the yscB gene.

TABLE 1

| Strains | HSA concentration (mg/L) |
| --- | --- |
| Strain F09 | 4.73 |
|  | 3.66 |
| Strain F09ΔyscB | 7.83 |
|  | 8.56 |

(3) Construction of Strains Expressing Trastuzumab

Strains expressing Trastuzumab were constructed from the *T. cellulolyticus* strains F09 and F09ΔyscB as parent strains according to the following procedure.

First, a DNA fragment for expressing Trastuzumab having a nucleotide sequence consisting of an upstream region of the creA gene of *T. cellulolyticus*, an upstream region of the cbh2 gene (cbh2 promoter; SEQ ID NO: 33) of *T. cellulolyticus*, a coding sequence of cbh1 secretion signal (SEQ ID NO: 34), a Trastuzumab-heavy chain gene (SEQ ID NO: 38), a downstream region of the cbh1 gene (cbh1 terminator; SEQ ID NO: 39) of *T. cellulolyticus*, a pyrF gene marker (SEQ ID NO: 37) of *T. cellulolyticus*, an upstream region of the cbh2 gene (cbh2 promoter; SEQ ID NO: 33) of *T. cellulolyticus*, a coding sequence of cbh1 secretion signal (SEQ ID NO: 34), a Trastuzumab-light chain gene (SEQ ID NO: 40), a downstream region of the cbh2 gene (cbh2 terminator; SEQ ID NO: 36) of *T. cellulolyticus*, and a downstream region of the creA gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 7 and 8, to amplify the upstream region of the creA gene, in combination with primers of SEQ ID NOS: 9 and 10, to amplify the upstream region of the cbh2 gene, in combination with primers of SEQ ID NOS: 11 and 21, to amplify the coding sequence of cbh1 secretion signal, in combination with primers of SEQ ID NOS: 22 and 23, to amplify the downstream region of the cbh1 gene, in combination with primers of SEQ ID NOS: 24 and 16, to amplify the downstream region of the pyrF gene marker, in combination with primers of SEQ ID NOS: 25 and 10, to amplify the upstream region of the cbh2 gene, in combination with primers of SEQ ID NOS: 11 and 26, to amplify the coding sequence of cbh1 secretion signal, in combination with primers of SEQ ID NOS: 13 and 14, to amplify the downstream region of the cbh2 gene, or in combination with primers of SEQ ID NOS: 27 and 18, to amplify the downstream region of the creA gene. Separately, PCR was performed by using a totally synthesized gene purchased from Eurofins as the template in combination with primers of SEQ ID NOS: 28 and 29, to amplify the Trastuzumab-heavy chain gene, or in combination with primers of SEQ ID NOS: 30 and 31, to amplify the Trastuzumab-light chain gene. The PCR products were purified by using Wizard SV Gel and PCR Clean-Up System (Promega). The purified PCR products were mutually ligated by repeating PCR using a mixture of each combination of two of the purified PCR products as the template, and incorporated by using In-Fusion HD Cloning Kit (Takara Bio) into a pUC plasmid included in the kit. *E. coli* JM109 was transformed with the reaction product, and cultured on LB agar medium containing 100 mg/L ampicillin at 37° C. overnight, to form colonies. A plasmid pUC-creA::Pcbh2-Her_H-pyrF-Pcbh2-Her_L, into which the DNA fragment for expressing Trastuzumab has been incorporated, was obtained from an obtained transformant by using Wizard Plus Miniprep System (Promega). PCR was performed by using the plasmid pUC-creA::Pcbh2-Her_H-pyrF-Pcbh2-Her_L as the template and primers of SEQ ID NOS: 7 and 18, to amplify the DNA fragment for expressing Trastuzumab, and the fragment was concentrated and purified by ethanol precipitation. Incidentally, ligation of the upstream and downstream regions of the creA gene at the respective ends of the Trastuzumab expressing sequence enables insertion of the Trastuzumab expressing sequence not into a random site of the genome but into the creA gene region as the target.

Then, the strains F09 and F09ΔyscB were each cultured and converted to protoplasts in a similar manner to Example (1), and transformed with the purified DNA fragment for expressing Trastuzumab in a similar manner to Example (1). The protoplasts were collected by centrifugation (2000 rpm for 10 minutes), inoculated into a minimal medium containing 1 M sucrose, and cultured at 30° C. for 7 days, to select strains of which the uracil auxotrophy was complemented. A colony that appeared was inoculated into a minimal medium and cultured at 30° C. for 4 days, and then replacement of the creA gene region with the Trastuzumab expressing sequence was confirmed, to obtain Trastuzumab expressing strains derived from the strains F09 and F09ΔyscB.

The Trastuzumab expressing strains derived from the strains F09 and F09ΔyscB were each inoculated into a culture medium containing 12 g/L Potato Dextrose Broth (Difco) and 20 g/L Bacto Agar (Difco), and cultured at 30° C. One agar disk excised from around the edge of a colony formed on the agar medium was inoculated into 20 mL of a liquid culture medium containing 50 g/L Solka Floc, 24 g/L KH$_2$PO$_4$, 5 g/L (NH$_4$)$_2$SO$_4$, 3 g/L Urea, 1 g/L Tween80, 1.2 g/L MgSO$_4$-7H$_2$O, 0.01 g/L ZnSO$_4$-7H$_2$O, 0.01 g/L MnSO$_4$-5H$_2$O, and 0.01 g/L CuSO$_4$-5H$_2$O, and cultured at 220 rpm at 30° C. for 7 days. The obtained culture broth was filtered with a 0.22 μm filter, to thereby obtain a culture supernatant.

In order to confirm secretory production of Trastuzumab, the obtained culture supernatant was subject to antibody purification by ProteinA using Proteus ProteinA Antibody Purification Midi Kit (BIO-RAD). Eluents obtained from equal volumes of the culture supernatants were subject to SDS-PAGE. Results are shown in FIG. 2. The Trastuzumab concentration in each sample was calculated by image analysis using serial dilutions of Trastuzumab standard (Chugai Pharmaceutical Co., Ltd.), which were electrophored at the same time, as a control. Results for a band corresponding to the light chain are shown in Table 2. A similar tendency to Table 2 was observed for a band corresponding to the heavy chain. It was confirmed that the strain F09ΔyscB provided an increase in the secretory production amount of Trastuzumab as compared with the strain F09, and hence, it was shown that the secretory production amount of Trastuzumab is improved by deletion of the yscB gene.

TABLE 2

| Strains | Trastuzumab concentration (g/L) |
|---|---|
| Strain F09 | 0.98 |
| Strain F09ΔyscB | 1.13 |

(4) Construction of Strains Expressing Nivolumab

Strains expressing nivolumab were constructed from the *T. cellulolyticus* strains F09 and F09ΔyscB as parent strains according to the following procedure.

First, a DNA fragment for expressing nivolumab having a nucleotide sequence consisting of an upstream region of the creA gene of *T. cellulolyticus*, an upstream region of the cbh2 gene (cbh2 promoter; SEQ ID NO: 33) of *T. cellulolyticus*, a coding sequence of cbh1 secretion signal (SEQ ID NO: 34), a nivolumab-heavy chain gene (SEQ ID NO: 45), a downstream region of the cbh1 gene (cbh1 terminator; SEQ ID NO: 39) of *T. cellulolyticus*, a pyrF gene marker (SEQ ID NO: 37) of *T. cellulolyticus*, an upstream region of the cbh2 gene (cbh2 promoter; SEQ ID NO: 33) of *T. cellulolyticus*, a coding sequence of cbh1 secretion signal (SEQ ID NO: 34), a nivolumab-light chain gene (SEQ ID NO: 46), a downstream region of the cbh2 gene (cbh2 terminator; SEQ ID NO: 36) of *T. cellulolyticus*, and a downstream region of the creA gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 7 and 8, to amplify the upstream region of the creA gene, in combination with primers of SEQ ID NOS: 9 and 10, to amplify the upstream region of the cbh2 gene, in combination with primers of SEQ ID NOS: 11 and 21, to amplify the coding sequence of cbh1 secretion signal, in combination with primers of SEQ ID NOS: 22 and 23, to amplify the downstream region of the cbh1 gene, in combination with primers of SEQ ID NOS: 24 and 16, to amplify the downstream region of the pyrF gene marker, in combination with primers of SEQ ID NOS: 25 and 10, to amplify the upstream region of the cbh2 gene, in combination with primers of SEQ ID NOS: 11 and 26, to amplify the coding sequence of cbh1 secretion signal, in combination with primers of SEQ ID NOS: 13 and 14, to amplify the downstream region of the cbh2 gene, or in combination with primers of SEQ ID NOS: 27 and 18, to amplify the downstream region of the creA gene. Separately, PCR was performed by using a totally synthesized gene purchased from Eurofins as the template in combination with primers of SEQ ID NOS: 47 and 48, to amplify the Nivolumab-heavy chain gene, or in combination with primers of SEQ ID NOS: 49 and 50, to amplify the nivolumab-light chain gene. The PCR products were purified by using Wizard SV Gel and PCR Clean-Up System (Promega). The purified PCR products were mutually ligated by repeating PCR using a mixture of each combination of two of the purified PCR products as the template, and incorporated by using In-Fusion HD Cloning Kit (Takara Bio) into a pUC plasmid included in the kit. E. coli JM109 was transformed with the reaction product, and cultured on LB agar medium containing 100 mg/L ampicillin at 37° C. overnight, to form colonies. A plasmid pUC-creA::Pcbh2-Opd_H-pyrF-Pcbh2-Opd_L, into which the DNA fragment for expressing nivolumab has been incorporated, was obtained from an obtained transformant by using Wizard Plus Miniprep System (Promega). PCR was performed by using the plasmid pUC-creA::Pcbh2-Opd_H-pyrF-Pcbh2-Opd_L as the template and primers of SEQ ID NOS: 7 and 18, to amplify the DNA fragment for expressing nivolumab, and the fragment was concentrated and purified by ethanol precipitation. Incidentally, ligation of the upstream and downstream regions of the creA gene at the respective ends of the nivolumab expressing sequence enables insertion of the nivolumab expressing sequence not into a random site of the genome but into the creA gene region as the target.

Then, the strains F09 and F09ΔyscB were each cultured and converted to protoplasts in a similar manner to Example (1), and transformed with the purified DNA fragment for expressing nivolumab in a similar manner to Example (1). The protoplasts were collected by centrifugation (2000 rpm for 10 minutes), inoculated into a minimal medium containing 1 M sucrose, and cultured at 30° C. for 7 days, to select strains of which the uracil auxotrophy was complemented. A colony that appeared was inoculated into a minimal medium and cultured at 30° C. for 4 days, and then replacement of the creA gene region with the Nivolumab expressing sequence was confirmed, to obtain nivolumab expressing strains derived from the strains F09 and F09ΔyscB.

The nivolumab expressing strains derived from the strains F09 and F09ΔyscB were each inoculated into a culture medium containing 12 g/L Potato Dextrose Broth (Difco) and 20 g/L Bacto Agar (Difco), and cultured at 30° C. One agar disk excised from around the edge of a colony formed on the agar medium was inoculated into 20 mL of a liquid culture medium containing 50 g/L Solka Floc, 24 g/L $KH_2PO_4$, 5 g/L $(NH_4)_2SO_4$, 3 g/L Urea, 1 g/L Tween80, 1.2 g/L $MgSO_4$-$7H_2O$, 0.01 g/L $ZnSO_4$-$7H_2O$, 0.01 g/L $MnSO_4$-$5H_2O$, and 0.01 g/L $CuSO_4$-$5H_2O$, and cultured at 220 rpm at 30° C. for 7 days. The obtained culture broth was filtered with a 0.22 μm filter, to thereby obtain a culture supernatant.

The secretory production amount of nivolumab was measured as the amount of human IgG in the culture supernatant by using Human IgG ELISA Quantitation Kit (Bethyl Laboratories, Inc.). Results are shown in Table 3. It was confirmed that the strain F09ΔyscB provided an increase in the secretory production amount of nivolumab as compared with the strain F09, and hence, it was shown that the secretory production amount of nivolumab is improved by deletion of the yscB gene.

TABLE 3

| Strains | nivolumab concentration (g/L) |
|---|---|
| Strain F09 | 1.07 |
| | 0.62 |
| Strain F09ΔyscB | 2.12 |
| | 2.11 |

(5) Construction of Strains Expressing Keratinocyte Growth Factor 1 (KGF-1) and Culture Evaluation Strains expressing keratinocyte growth factor 1 (KGF-1) were constructed from the *T. cellulolyticus* strains F09 and F09ΔyscB as parent strains according to the following procedure.

First, a DNA fragment for expressing KGF-1 having a nucleotide sequence consisting of an upstream region of the creA gene of *T. cellulolyticus*, an upstream region of the cbh2 gene (cbh2 promoter; SEQ ID NO: 33) of *T. cellulolyticus*, a coding sequence of cbh1 secretion signal (SEQ ID NO: 34), a gene encoding KGF-1 added with a His6 tag (SEQ ID NO: 51), a downstream region of the cbh2 gene (cbh2 terminator; SEQ ID NO: 36) of *T. cellulolyticus*, a pyrF gene marker (SEQ ID NO: 37) of *T. cellulolyticus*, and a downstream region of the creA gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 7 and 8, to amplify the upstream region of the creA gene, in combination with primers of SEQ ID NOS: 9 and 10, to amplify the upstream region of the cbh2 gene, in combination with primers of SEQ ID NOS: 11 and 12, to amplify the coding sequence of cbh1 secretion signal, in combination with primers of SEQ ID NOS: 13 and 14, to amplify the downstream region of the cbh2 gene, in combination with primers of SEQ ID NOS: 15 and 16, to amplify the downstream region of the pyrF gene marker, or in combination with primers of SEQ ID NOS: 17 and 18, to amplify the downstream region of the creA gene. Separately, PCR was performed by using a totally synthesized gene purchased from Eurofins as the template and primers of SEQ ID NOS: 52 and 53, to amplify the gene encoding KGF-1 added with a His6 tag. The PCR products were purified by using Wizard SV Gel and PCR Clean-Up System (Promega). The purified PCR products were mutually ligated by repeating PCR using a mixture of each combination of two of the purified PCR products as the template, and incorporated by using In-Fusion HD Cloning Kit (Takara Bio) into a pUC plasmid included in the kit. *E. coli* JM109 was transformed with the reaction product, and cultured on LB agar medium containing 100 mg/L ampicillin at 37° C. overnight, to form colonies. A plasmid pUC-creA::Pcbh2-KGF-1-pyrF, into which the DNA fragment for expressing KGF-1 has been incorporated, was obtained from an obtained transformant by using Wizard Plus Miniprep System (Promega). PCR was performed by using the plasmid pUC-creA::Pcbh2-KGF-1-pyrF as the template and primers of SEQ ID NOS: 7 and 18, to amplify the DNA fragment for expressing KGF-1, and the fragment was concentrated and purified by ethanol precipitation. Incidentally, ligation of the upstream and downstream regions of the creA gene at the respective ends of the KGF-1 expressing sequence enables insertion of the KGF-1 expressing sequence not into a random site of the genome but into the creA gene region as the target.

Then, the strains F09 and F09ΔyscB were each cultured and converted to protoplasts in a similar manner to Example (1), and transformed with the purified DNA fragment for expressing KGF-1 in a similar manner to Example (1). The protoplasts were collected by centrifugation (2000 rpm for 10 minutes), inoculated into a minimal medium containing 1 M sucrose, and cultured at 30° C. for 7 days, to select strains of which the uracil auxotrophy was complemented. A colony that appeared was inoculated into a minimal medium and cultured at 30° C. for 4 days, and then replacement of the creA gene region with the KGF-1 expressing sequence was confirmed, to obtain KGF-1 expressing strains derived from the strains F09 and F09ΔyscB.

The KGF-1 expressing strains derived from the strains F09 and F09ΔyscB were each inoculated into a culture medium containing 12 g/L Potato Dextrose Broth (Difco) and 20 g/L Bacto Agar (Difco), and cultured at 30° C. One agar disk excised from around the edge of a colony formed on the agar medium was inoculated into 20 mL of a liquid culture medium containing 50 g/L Solka Floc, 24 g/L $KH_2PO_4$, 5 g/L $(NH_4)_2SO_4$, 3 g/L Urea, 1 g/L Tween80, 1.2 g/L $MgSO_4$-$7H_2O$, 0.01 g/L $ZnSO_4$-$7H_2O$, 0.01 g/L $MnSO_4$-$5H_2O$, and 0.01 g/L $CuSO_4$-$5H_2O$, and cultured at 220 rpm at 30° C. for 7 days. The obtained culture broth was filtered with a 0.22 μm filter, to thereby obtain a culture supernatant.

In order to confirm secretory production of KGF-1, the obtained culture supernatant was subject to His-tag purification using Ni-NTA Agarose (QIAGEN), and the purified product was subject to SDS-PAGE. Specifically, the culture supernatant adjusted to pH8.0 was added with Ni-NTA Agarose (QIAGEN) and mixed for 1 hour, then washed with 50 mM phosphate buffer (pH8.0), added with a SDS-PAGE sample buffer, and heated at 95° C. for 5 minutes, and the supernatant was subject to SDS-PAGE. Results are shown in FIG. 3. It was confirmed that the strain F09ΔyscB provided an increase in the secretory production amount of KGF-1 as compared with the strain F09, and hence, it was shown that the secretory production amount of KGF-1 is improved by deletion of the yscB gene.

(6) Construction of Strains Expressing Vascular Endothelial Growth Factor (VEGF) and Culture Evaluation Strains expressing vascular endothelial growth factor (VEGF) were constructed from the *T. cellulolyticus* strains F09 and F09ΔyscB as parent strains according to the following procedure.

First, a DNA fragment for expressing VEGF having a nucleotide sequence consisting of an upstream region of the creA gene of *T. cellulolyticus*, an upstream region of the cbh2 gene (cbh2 promoter; SEQ ID NO: 33) of *T. cellulolyticus*, a coding sequence of cbh1 secretion signal (SEQ ID NO: 34), a gene encoding VEGF added with a His6 tag (SEQ ID NO: 54), a downstream region of the cbh2 gene (cbh2 terminator; SEQ ID NO: 36) of *T. cellulolyticus*, a pyrF gene marker (SEQ ID NO: 37) of *T. cellulolyticus*, and a downstream region of the creA gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 7 and 8, to amplify the upstream region of the creA gene, in combination with primers of SEQ ID NOS: 9 and 10, to amplify the upstream region of the cbh2 gene, in combination with primers of SEQ ID NOS: 11 and 12, to amplify the coding sequence of cbh1 secretion signal, in combination with primers of SEQ ID NOS: 13 and 14, to amplify the downstream region of the cbh2 gene, in combination with primers of SEQ ID NOS: 15 and 16, to amplify the downstream region of the pyrF gene marker, or in combination with primers of SEQ ID NOS: 17 and 18, to amplify the downstream region of the creA gene. Separately, PCR was performed by using a totally synthesized gene purchased from Eurofins as the template and primers of SEQ ID NOS: 55 and 56, to amplify the gene encoding VEGF added with a His6 tag. The PCR products were purified by using Wizard SV Gel and PCR Clean-Up System (Promega). The purified PCR products were mutually ligated by repeating PCR using a mixture of each combination of two of the purified PCR products as the template, and incorporated by using In-Fusion HD Cloning Kit (Takara Bio) into a pUC plasmid included in the kit. *E. coli* JM109 was transformed with the reaction product, and cultured on LB agar medium containing 100 mg/L ampicillin at 37° C. overnight, to form colonies. A plasmid pUC-creA::Pcbh2-VEGF-pyrF, into which the DNA fragment for expressing VEGF has been incorporated, was obtained from an obtained transformant by using Wizard Plus Miniprep System (Promega). PCR was performed by using the plasmid pUC-creA::Pcbh2-VEGF-pyrF as the template and primers of SEQ ID NOS: 7 and 18, to amplify the DNA fragment for expressing VEGF, and the fragment was concentrated and purified by ethanol precipitation. Incidentally, ligation of the upstream and downstream regions of the creA gene at the respective ends of the VEGF expressing sequence enables insertion of the VEGF expressing sequence not into a random site of the genome but into the creA gene region as the target.

Then, the strains F09 and F09ΔyscB were each cultured and converted to protoplasts in a similar manner to Example (1), and transformed with the purified DNA fragment for expressing VEGF in a similar manner to Example (1). The protoplasts were collected by centrifugation (2000 rpm for 10 minutes), inoculated into a minimal medium containing 1 M sucrose, and cultured at 30° C. for 7 days, to select strains in which the uracil auxotrophy was complemented. A colony that appeared was inoculated into a minimal medium and cultured at 30° C. for 4 days, and then replacement of the creA gene region with the VEGF expressing sequence was confirmed, to obtain VEGF expressing strains derived from the strains F09 and F09ΔyscB.

The VEGF expressing strains derived from the strains F09 and F09ΔyscB were each inoculated into a culture medium containing 12 g/L Potato Dextrose Broth (Difco) and 20 g/L Bacto Agar (Difco), and cultured at 30° C. One agar disk excised from around the edge of a colony formed on the agar medium was inoculated into 20 mL of a liquid culture medium containing 50 g/L Solka Floc, 24 g/L $KH_2PO_4$, 5 g/L $(NH_4)_2SO_4$, 3 g/L Urea, 1 g/L Tween80, 1.2 g/L $MgSO_4$-$7H_2O$, 0.01 g/L $ZnSO_4$-$7H_2O$, 0.01 g/L $MnSO_4$-$5H_2O$, and 0.01 g/L $CuSO_4$-$5H_2O$, and cultured at 220 rpm at 30° C. for 7 days. The obtained culture broth was filtered with a 0.22 μm filter, to thereby obtain a culture supernatant.

In order to confirm secretory production of VEGF, the obtained culture supernatant was subject to His-tag purification using Ni-NTA Agarose (QIAGEN), and the purified product was subject to SDS-PAGE. Specifically, the culture supernatant adjusted to pH8.0 was added with Ni-NTA Agarose (QIAGEN) and mixed for 1 hour, then washed with 50 mM phosphate buffer (pH8.0), added with a SDS-PAGE sample buffer, and heated at 95° C. for 5 minutes, and the supernatant was subject to SDS-PAGE. Results are shown in FIG. 4. It was confirmed that the strain F09ΔyscB provided an increase in the secretory production amount of VEGF as compared with the strain F09, and hence, it was shown that the secretory production amount of VEGF is improved by deletion of the yscB gene.

(7) Analysis of Protease Involved in Degradation of Heterologous Proteins (7-1) Analysis of Localization of Protease Involved in Degradation of Heterologous Proteins As described above, when producing a heterologous protein HSA by secretory production using the *T. cellulolyticus* strain F09 (Japanese Patent Laid-open (Kokai) No. 2016-131533) as a host in (2), degradation of HSA was observed (FIG. 1). Hence, in order to investigate localization of a protease involved in degradation of heterologous proteins, a culture supernatant of the strain F09 was prepared as follows. First, the strain F09 was inoculated into a culture medium containing 12 g/L Potato Dextrose Broth (Difco) and 20 g/L Bacto Agar (Difco), and cultured at 30° C. One agar disk excised from around the edge of a colony formed on the agar medium was inoculated into 20 mL of a liquid culture medium containing 50 g/L Solka Floc, 24 g/L $KH_2PO_4$, 5 g/L $(NH_4)_2SO_4$, 3 g/L Urea, 1 g/L Tween80, 1.2 g/L $MgSO_4$-$7H_2O$, 0.01 g/L $ZnSO_4$-$7H_2O$, 0.01 g/L $MnSO_4$-$5H_2O$, 0.01 g/L $CuSO_4$-$5H_2O$, 1 g/L Uracil, and 1 g/L Uridine, and cultured at 220 rpm at 30° C. for 7 days. The obtained culture broth was filtered with a 0.22 μm filter to remove cells, to thereby obtain a culture supernatant. The culture supernatant was mixed with a purified HSA (Abcam, ab201876), and left to stand at 30° C. for 3 days. Then, the mixture was subject to SDS-PAGE, followed by Western blotting using an anti-HSA antibody (SIGMA, A6684). Results are shown in FIG. 5. Since a plurality of bands corresponding to degradation products were observed at positions of molecular weights smaller than that of HSA, degradation of HSA was confirmed. From these results, it was suggested that the culture supernatant of the strain F09 contains a protease involved in degradation of heterologous proteins.

(7-2) Extraction of Candidate Genes of Protease Involved in Degradation of Heterologous Proteins In order to extract candidate genes of protease involved in degradation of heterologous proteins, cells of the strain F09 were collected from the culture broth obtained in (7-1) by centrifugation (5000 rpm, 5 minutes), and total RNA was extracted by using RNeasy Plant Mini Kit (QIAGEN). A library was prepared from the obtained total RNA by using TruSeq Stranded mRNA SamplePrep Kit (illumina), and expression analysis was carried out by using a next generation sequencer MiSeq in combination with MiSeq Reagent Kit v2 500 cycle (illumina). Genes annotated as protease were extracted, and those sorted in the order of the expression amount (i.e. mapped read number) are shown in Table 4. Since the cbh1 gene showing the highest expression amount provided 140,000 reads and the cbh2 gene showing the second-highest expression amount provided 80,000 reads, genes providing 800 reads or below were excluded. The five genes shown in Table 4 were extracted as candidate genes of protease. Although it was suggested in (7-1) that the culture supernatant contains a protease, considering elution of the protease due to cell lysis and mistake of annotation, all these five genes were used as candidates for the following investigation without considering localization based on annotation.

TABLE 4

| Read number | Gene name | Annotation |
|---|---|---|
| 5112 | Pepsin 1 | Pepsin-like proteinases secreted from pathogens to degrade host proteins |
| 3391 | yscB | Vacuolar proteinase B (yscB), a serine protease of the subtilisin family |
| 2676 | CPY | Vacuolar carboxypeptidase Y (proteinase C); member of the serine carboxypeptidase family |
| 1142 | Pepsin2 | Pepsin-like proteinases secreted from pathogens to degrade host proteins |
| 861 | Thermolysin | Thermolysin metallopeptidase |

(7-3) Construction of Strains Deficient in Extracted Protease Candidate Genes

Strains deficient in the respective protease candidate genes derived from *T. cellulolyticus* F09 were constructed from the *Talaromyces cellulolyticus* strain F09 (Japanese Patent Laid-open (Kokai) No. 2016-131533) as a parent strain by disruption of the respective protease candidate genes (pepsin1, SEQ ID NO: 57; yscB, SEQ ID NO: 32; CPY, SEQ ID NO: 58; pepsin2, SEQ ID NO: 59; and thermolysin, SEQ ID NO: 60) according to the following procedure. The strain F09 has a mutation (single nucleotide substitution) in a pyrF gene obtained from the *T. cellulolyticus* strain S6-25 (NITE BP-01685) as a parent strain. The strain F09 shows uracil auxotrophy due to the mutation in the pyrF gene.

First, a DNA fragment for protease candidate gene disruption having a nucleotide sequence consisting of an upstream region of each protease candidate gene of *T. cellulolyticus*, a hygromycin-resistant gene, and a downstream region of each protease candidate gene of *T. cellulolyticus* ligated in this order was prepared according to the following procedure.

PCR was performed by using the genomic DNA of the *T. cellulolyticus* strain Y-94 (FERM BP-5826) as the template in combination with primers of SEQ ID NOS: 61 and 62, to amplify the upstream region of the pepsin1 gene, in combination with primers of SEQ ID NOS: 63 and 64, to amplify the downstream region of the pepsin1 gene, in combination with primers of SEQ ID NOS: 1 and 65, to amplify the upstream region of the yscB gene, in combination with primers of SEQ ID NOS: 66 and 4, to amplify the downstream region of the yscB gene, in combination with primers of SEQ ID NOS: 67 and 68, to amplify the upstream region of the CPY gene, in combination with primers of SEQ ID NOS: 69 and 70, to amplify the downstream region of the CPY gene, in combination with primers of SEQ ID NOS: 71 and 72, to amplify the upstream region of the pepsin2 gene, in combination with primers of SEQ ID NOS: 73 and 74, to amplify the downstream region of the pepsin2 gene, in combination with primers of SEQ ID NOS: 75 and 76, to amplify the upstream region of the thermolysin gene, or in combination with primers of SEQ ID NOS: 77 and 78, to amplify the downstream region of the thermolysin gene. Separately, PCR was performed by using the genomic DNA of the *T. cellulolyticus* strain Y-94 (FERM BP-5826) as the template and primers of SEQ ID NOS: 79 and 80, to amplify the pyrF gene (including promoter and terminator). The PCR products were each purified by using Wizard SV Gel and PCR Clean-Up System (Promega). In-Fusion HD Cloning Kit (Takara Bio) was used to incorporate the purified PCR products of the upstream region, the downstream region, and the pyrF gene into a pUC plasmid included in the kit and to thereby ligate them. *E. coli* JM109 was transformed with the reaction product, and cultured on LB agar medium containing 100 mg/L ampicillin at 37° C. overnight, to form colonies. Plasmids into which the respective DNA fragments for protease candidate gene disruption have been incorporated were each obtained from an obtained transformant by using Wizard Plus Miniprep System (Promega). PCR was performed by using each of the plasmids as the template and primers (SEQ ID NOS: 61 and 64 for pepsin1, SEQ ID NOS: 1 and 4 for YscB, SEQ ID NOS: 67 and 70 for CPY, SEQ ID NOS: 71 and 74 for pepsin2, SEQ ID NOS: 75 and 78 for thermolysin) to amplify the DNA fragment for protease candidate gene disruption, and the fragment was concentrated and purified by ethanol precipitation.

Then, the strain F09 was inoculated into a culture medium containing 12 g/L Potato Dextrose Broth (Difco) and 20 g/L Bacto Agar (Difco), and cultured at 30° C. One agar disk excised from around the edge of a colony formed on the agar medium was inoculated into a culture medium containing 24 g/L Potato Dextrose Broth, and gyratory culture (220 rpm) was carried out at 30° C. for 2 days. Cells were collected by centrifugation (5000 rpm for 5 minutes), and added with 30 mL of a solution containing 10 g/L Yatalase (Takara Bio), 10 mM $KH_2PO_4$, and 0.8 M NaCl (pH6.0). Reaction was carried out at 30° C. for 2 hours with shaking, to digest cell walls and prepare protoplasts. After residues were removed by using a glass filter, protoplasts were collected by centrifugation (2000 rpm for 10 minutes), and suspended with Tris-HCl buffer (pH7.5) containing 1.2 M Sorbitol and 10 mM $CaCl_2$), to prepare 1 mL of a protoplast solution. A 200-μL aliquot of the protoplast solution was mixed with 10 μg of each of the purified DNA fragments for protease candidate gene disruption, and 50 μL of Tris-HCl buffer (pH7.5) containing 400 g/L PEG4000 and 10 mM $CaCl_2$), and left on ice for 30 minutes. Then, the mixture was further mixed with 1 mL of Tris-HCl buffer (pH7.5) containing 400 g/L PEG4000 and 10 mM $CaCl_2$), and left at a room temperature for 15 minutes to allow transformation. Protoplasts were collected by centrifugation (2000 rpm for 10 minutes), inoculated into a minimal medium (10 g/L Glucose, 10 mM $NH_4Cl$, 10 mM $KH_2PO_4$, 7 mM KCl, 2 mM $MgSO_4$, 0.06 mg/L $H_3BO_3$, 0.26 mg/L $(NH_4)_6Mo_7O_{24}$-$4H_2O$, 1 mg/L $FeCl_3$-$6H_2O$, 0.4 mg/L $CuSO_4$-$5H_2O$, 0.08 mg/L $MnCl_2$, 2 mg/L $ZnCl_2$, and 20 g/L Bacto Agar) containing 1 M sucrose, cultured at 30° C. for 7 days, to select strains of which the uracil auxotrophy was complemented. A colony that appeared was inoculated into a minimal medium and cultured at 30° C. for 4 days, and then replacement of the protease candidate gene region with the pyrF gene was confirmed, to obtain strains deficient in the respective protease candidate genes derived from the strain F09.

(7-4) Evaluation of Protease Activity in Culture Supernatants of Strains Deficient in Protease Candidate Genes The strains deficient in the respective protease candidate genes were each inoculated into a culture medium containing 12 g/L Potato Dextrose Broth (Difco) and 20 g/L Bacto Agar (Difco), and cultured at 30° C. One agar disk excised from around the edge of a colony formed on the agar medium was inoculated into 20 mL of a liquid culture medium containing 50 g/L Solka Floc, 24 g/L $KH_2PO_4$, 5 g/L $(NH_4)_2SO_4$, 3 g/L Urea, 1 g/L Tween80, 1.2 g/L $MgSO_4$-$7H_2O$, 0.01 g/L $ZnSO_4$-$7H_2O$, 0.01 g/L $MnSO_4$-$5H_2O$, and 0.01 g/L $CuSO_4$-$5H_2O$, and cultured at 220 rpm at 30° C. for 7 days. The obtained culture broth was filtered with a 0.22 μm filter, to thereby obtain a culture supernatant. The culture supernatant was mixed with a purified HSA and protease activity was evaluated in a similar manner to (7-1). Results are shown in FIG. 6. In the cases of the strains deficient in pepsin1, CPY, pepsin2, and thermolysin-deletion, since a plurality of bands corresponding to degradation products were observed at positions of molecular weights smaller than that of HSA as with the case of the strain F09, degradation of HSA was confirmed. By contrast, in the case of the strain deficient in yscB, the bands corresponding to degradation products were eliminated. From these results, it was revealed that YscB is a protease responsible for degradation of heterologous proteins in the culture supernatant of the strain F09.

INDUSTRIAL APPLICABILITY

According to the present invention, a protein can be efficiently produced.

<Explanation of Sequence Listing>
SEQ ID NOS:
1-31: Primers
32: Nucleotide sequence of yscB gene of *Talaromyces cellulolyticus* strain S6-25
33: Nucleotide sequence of cbh2 promoter of *Talaromyces cellulolyticus*
34: Nucleotide sequence encoding Cbh1 signal peptide of *Talaromyces cellulolyticus*
35: Amino acid sequence of human serum albumin (HSA)
36: Nucleotide sequence of cbh2 terminator
37: Nucleotide sequence of pyrF gene marker of *Talaromyces cellulolyticus*
38: Nucleotide sequence of Trastuzumab-heavy chain gene
39: Nucleotide sequence of cbh1 terminator
40: Nucleotide sequence of Trastuzumab-light chain gene
41: Nucleotide sequence of cbh1 promoter of *Talaromyces cellulolyticus*
42: Amino acid sequence of Cbh1 signal peptide of *Talaromyces cellulolyticus*
43: Amino acid sequence of YscB protein of *Talaromyces cellulolyticus* strain S6-25
44: Nucleotide sequence of creA gene of *Talaromyces cellulolyticus* strain S6-25
45: Nucleotide sequence of Nivolumab-heavy chain gene
46: Nucleotide sequence of Nivolumab-light chain gene
47-50: Primers
51: Nucleotide sequence of Keratinocyte growth factor 1 (KGF-1) gene
52-53: Primers
54: Nucleotide sequence of Vascular endothelial growth factor (VEGF) gene
55-56: Primers
57: Nucleotide sequence of Pepsin1 gene
58: Nucleotide sequence of CPY gene
59: Nucleotide sequence of Pepsin2 gene
60: Nucleotide sequence of Thermolysin gene
61-80: Primers

The invention claimed is:

1. A method for producing an objective protein, comprising culturing *Talaromyces cellulolyticus* having an ability to produce an objective protein in a culture medium, wherein the *Talaromyces cellulolyticus* has been modified so that the protease activity of a YscB protein is reduced as compared with a non-modified *Talaromyces cellulolyticus*;

wherein the YscB protein is selected from the group consisting of:

(a) a protein comprising the amino acid sequence of SEQ ID NO: 43;

(b) a protein comprising the amino acid sequence of SEQ ID NO: 43, but which includes substitution, deletion, insertion, and/or addition of 1 to 10 amino acid residues, and wherein said protein has a protease activity; and (c) a protein comprising an amino acid sequence having an identity of 95% or higher to the amino acid sequence of SEQ ID NO: 43, and wherein said protein has a protease activity.

2. The method according to claim 1, wherein the activity of the YscB protein is reduced by reducing the expression of a yscB gene or disrupting a yscB gene.

3. The method according to claim 1, wherein the activity of the YscB protein is reduced by deletion of ayscB gene.

4. The method according to claim 1, wherein the *Talaromyces cellulolyticus* has been modified so that the activity of a CreA protein is reduced as compared with a non-modified *Talaromyces cellulolyticus*.

5. The method according to claim 4, wherein the activity of the CreA protein is reduced by reducing the expression of a creA gene or disrupting a creA gene.

6. The method according to claim 4, wherein the activity of the CreA protein is reduced by deletion of a creA gene.

7. The method according to claim 1, wherein the *Talaromyces cellulolyticus* is derived from *Talaromyces cellulolyticus* strain S6-25 (NITE BP-01685).

8. The method according to claim 1, further comprising collecting the objective protein.

9. The method according to claim 1, wherein the objective protein is accumulated in the culture medium by the culturing.

10. The method according to claim 1, wherein the objective protein is expressed as a fused protein with a signal peptide that functions in *Talaromyces cellulolyticus*.

11. The method according to claim 1, wherein the objective protein is a heterologous protein.

12. The method according to claim 1, wherein the objective protein is a protein derived from human.

13. The method according to claim 1, wherein the objective protein is human serum albumin.

14. The method according to claim 1, wherein the objective protein is an antibody-related molecule.

15. The method according to claim 1, wherein the objective protein is a growth factor.

* * * * *

SEQUENCE LISTING

<160> NUMBER OF SEQ ID NOS: 80

<210> SEQ ID NO 1
<211> LENGTH: 40

```
<212> TYPE: DNA
<213> ORGANISM: Artificial Sequence
<220> FEATURE:
<223> OTHER INFORMATION: primer

<400> SEQUENCE: 1
cggtacccgg ggatcttggg gcacagagac aacagggtca                               40

<210> SEQ ID NO 2
<211> LENGTH: 40
<212> TYPE: DNA
<213> ORGANISM: Artificial Sequence
<220> FEATURE:
<223> OTHER INFORMATION: primer

<400> SEQUENCE: 2
agatagggtt gagtgagata gcgtgagcac actgagcagg                               40

<210> SEQ ID NO 3
<211> LENGTH: 40
<212> TYPE: DNA
<213> ORGANISM: Artificial Sequence
<220> FEATURE:
<223> OTHER INFORMATION: primer

<400> SEQUENCE: 3
aaagtgtaaa gcctgcaaca cgctacctct tccacagtag                               40

<210> SEQ ID NO 4
<211> LENGTH: 40
<212> TYPE: DNA
<213> ORGANISM: Artificial Sequence
<220> FEATURE:
<223> OTHER INFORMATION: primer

<400> SEQUENCE: 4
cgactctaga ggatcgagct gattgagcat gctaacgcag                               40

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
cactcaaccc tatctcggtc t                                                   21

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
caggctttac actttatgct tccg                                                24

<210> SEQ ID NO 7
<211> LENGTH: 40
<212> TYPE: DNA
<213> ORGANISM: Artificial Sequence
<220> FEATURE:
<223> OTHER INFORMATION: primer

<400> SEQUENCE: 7
```

```
cggtacccgg ggatcagcgc agaccaatgc cagaggagaa                          40
```

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8

```
gcgcgagttg cgcgatgaaa tttat                                         25
```

<210> SEQ ID NO 9
<211> LENGTH: 40
<212> TYPE: DNA
<213> ORGANISM: Artificial Sequence
<220> FEATURE:
<223> OTHER INFORMATION: primer

<400> SEQUENCE: 9

```
tcgcgcaact cgcgctgcta tgcagttgat gctactgtgt                          40
```

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10

```
agttgctaaa tgatcaagaa gcttcacttt                                    30
```

<210> SEQ ID NO 11
<211> LENGTH: 45
<212> TYPE: DNA
<213> ORGANISM: Artificial Sequence
<220> FEATURE:
<223> OTHER INFORMATION: primer

<400> SEQUENCE: 11

```
acagctggtg ctcagaagtg ggtcaccttc atctctctcc tcttc                    45
```

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12

```
ctgagcacca gctgttgcca gcaag                                         25
```

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13

```
tagatcagct ttgagtgcag caaaa                                         25
```

<210> SEQ ID NO 14
<211> LENGTH: 27
<212> TYPE: DNA
<213> ORGANISM: Artificial Sequence

```
<220> FEATURE:
<223> OTHER INFORMATION: primer

<400> SEQUENCE: 14
gcttgtttga gaatacatga ggttgcc                                            27

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
tattctcaaa caagcgtcaa ttcagatcgg ctgccgcctg                               40

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
ataagtgaac gccgagtcag tacta                                              25

<210> SEQ ID NO 17
<211> LENGTH: 40
<212> TYPE: DNA
<213> ORGANISM: Artificial Sequence
<220> FEATURE:
<223> OTHER INFORMATION: primer

<400> SEQUENCE: 17
tcggcgttca cttatcctct ttctcgccct ttcttctcaa                               40

<210> SEQ ID NO 18
<211> LENGTH: 40
<212> TYPE: DNA
<213> ORGANISM: Artificial Sequence
<220> FEATURE:
<223> OTHER INFORMATION: primer

<400> SEQUENCE: 18
cgactctaga ggatcaaccg tcgatcagaa ggagcgcaat                               40

<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19
acagctggtg ctcagaagtg ggtcaccttc atctctctcc                               40

<210> SEQ ID NO 20
<211> LENGTH: 40
<212> TYPE: DNA
<213> ORGANISM: Artificial Sequence
<220> FEATURE:
<223> OTHER INFORMATION: primer

<400> SEQUENCE: 20
ctcaaagctg atctacaaac caagagcagc ttgactagcg                               40
```

<210> SEQ ID NO 21
<211> LENGTH: 40
<212> TYPE: DNA
<213> ORGANISM: Artificial Sequence
<220> FEATURE:
<223> OTHER INFORMATION: primer

<400> SEQUENCE: 21
gacgagctgg acttcctgag caccagctgt tgccagcaag          40

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
taaattttca cttctttctt cgcctattga          30

<210> SEQ ID NO 23
<211> LENGTH: 45
<212> TYPE: DNA
<213> ORGANISM: Artificial Sequence
<220> FEATURE:
<223> OTHER INFORMATION: primer

<400> SEQUENCE: 23
ccgatctgaa ttgacccgaa aacggtaagg cgtagttata gaaat          45

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
gtcaattcag atcggctgcc gcctg          25

<210> SEQ ID NO 25
<211> LENGTH: 40
<212> TYPE: DNA
<213> ORGANISM: Artificial Sequence
<220> FEATURE:
<223> OTHER INFORMATION: primer

<400> SEQUENCE: 25
tcggcgttca cttattgcta tgcagttgat gctactgtgt          40

<210> SEQ ID NO 26
<211> LENGTH: 40
<212> TYPE: DNA
<213> ORGANISM: Artificial Sequence
<220> FEATURE:
<223> OTHER INFORMATION: primer

<400> SEQUENCE: 26
tgtcatctgg atgtcctgag caccagctgt tgccagcaag          40

<210> SEQ ID NO 27
<211> LENGTH: 40
<212> TYPE: DNA
<213> ORGANISM: Artificial Sequence
<220> FEATURE:
<223> OTHER INFORMATION: primer

<400> SEQUENCE: 27
tattctcaaa caagccctct ttctcgccct ttcttctcaa                                40

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
gaagtccagc tcgtcgagtc tggtg                                               25

<210> SEQ ID NO 29
<211> LENGTH: 37
<212> TYPE: DNA
<213> ORGANISM: Artificial Sequence
<220> FEATURE:
<223> OTHER INFORMATION: primer

<400> SEQUENCE: 29
agaagtgaaa atttatttac caggagacaa ggacaga                                  37

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
gacatccaga tgacacagtc ccctt                                               25

<210> SEQ ID NO 31
<211> LENGTH: 40
<212> TYPE: DNA
<213> ORGANISM: Artificial Sequence
<220> FEATURE:
<223> OTHER INFORMATION: primer

<400> SEQUENCE: 31
ctcaaagctg atctaacact caccacggtt gaaggactta                               40

<210> SEQ ID NO 32
<211> LENGTH: 1589
<212> TYPE: DNA
<213> ORGANISM: Talaromyces cellulolyticus

<400> SEQUENCE: 32
atgaagggcg tcctcagcct ttcgctgctg ccgttgttga cggttgcgtc accggtgatg         60
ccgcgcacca tccacaacga cgctgctccc attctctctt cgtccaacgc cgttgaggtc        120
ccagattcat atatcattgt ctttaaagac catgtagatt ctgcttctgc cgcagcccat        180
cataactggg tgcaagacat tcacagccaa cacaccgagc tccgaaagcg gtctcaattc        240
ccattcgctg acaatgcctt tgccggtctc aaacacactt ttgacattgc cggcagcttc        300
cttggttact caggacactt cgaagagaat gtcattgagg ccattcgccg acaccccgat        360
gtgagttatc cgcacgtgcc ctactcctaa ggcaatgact aatacgcatc tccacctata        420
ggttgattac atcgagaagg attctcttgt ccacaccatg gaaatcccg ccccttgagaa        480 gaacgcccca tggggtttgg ctcgtatttc gcaccgtgag agcttgagct tcggaagctt        540

```
caacaagtac ttgtacgctg ccgacggcgg tgaaggtgtt gacgtttatg tcattgacac    600
tggtaccaac atcgaccacg tcgacttcga gggtcgtgct tcctggggca agaccatccc    660
cactgacgat gaggatgttg atggcaatgg tcacggtact cactgctccg gaactattgc    720
gggcaagaag tacggtgttg ccaagaaggc caatgtctac gctgtcaagg tcttgaagtc    780
taacggttct ggaaccatgt ccgatgtcgt tcagggtgtc gaatgggctg ctactcagca    840
catcaagaag gtcaaggacg ccaaggccgg aaaagccaag ggcttcaagg gtagcgctgc    900
gaacatgagt ctcggtggtg gcaagtccgt cactcttgac aaggctgtca atgctgctgt    960
tgatgctggt atccacttcg ctgtcgctgc tggcaacgac aacgccgact cctgcaacta   1020
ctcccctgcc gccgctgaga aggccgtcac cgtcggagcc tcgaccttgg ccgatgagcg   1080
tgcttacttc tccaactacg gcaagtgcaa cgacatcttt gctcctggtc tgaacattct   1140
ctctacctgg atcggcagca agtacgccgt caacaccatc tccggtacct ccatggcttc   1200
tcctcacatt gctggtcttt tggcctactt cctctctctc cagcctgcca gtgactccgc   1260
cttcgctgtt gccgagatta ctcccaagaa gttgaaggag aacctcattg ctattggtac   1320
ccagggcgct cttactgatg ttccctctga caccactaac gtaagttgac tctgttagtc   1380
tttcaatgca ttatcaacta caactgtgt catagattct cgcctggaac ggtggtggct    1440
cagccaacta caccgacatc attgcccaag gtggttacaa gaccaagaca ctcagcaacg   1500
aagttgacga attgatcaac aagttggagg tcgtgaacga ggaactcggt gccatctaca   1560
gccacatcaa ggatgccatt gccgcataa                                     1589

<210> SEQ ID NO 33
<211> LENGTH: 1100
<212> TYPE: DNA
<213> ORGANISM: Talaromyces cellulolyticus

<400> SEQUENCE: 33
tgctatgcag ttgatgctac tgtgttctaa ataattgat agggttaggg tcgggtataa      60
ggcgatgcaa tgtatcaatt atcacgagaa ataatgcaga aaaacacaat tccccgtatc    120
tgttgattct taaacaatct gatcaccaat ttgtagaaag aaacgattat aaggtgccat    180
ggtaatgctg gagtttacac aggatactac ttgttctgtt cattacaatg aaccgtaatt    240
gcattctgtt ttgaccactc aacaaatcct acacaaaagt aagtggactt cagtgctcgc    300
tctacgcaag taaatacttg gcatatatgg cctcgtatat tcttacaatg aggtaaattc    360
cgatagatta ctgcccaact agtcaatctt aaatccttaa gagatacagg gggaggcgga    420
agtacctgaa accacgtaat aagacgttca gggtcatgtg aatgtatgta gtatccatgt    480
ccaatacaat tgataatagt atccagtatt atatctcatt caggtaagcg ccacgcgatt    540
cttcagatct acttaactgc cgactcgcca aacgaaacaa cgtttattcg tgaccccaga    600
aaatcaccgc ggagttgcgg aggaccagtt tgtacaatgc accgaaccaa gcgttggtca    660
tttttctgga aatgggccaa acgttagaag tgattggtca gagctacatc tgaaggtgaa    720
gcaatttccg gtatgcatac atgacagcaa gcttacctac caagaccaag ttattcccca    780
gcatttgccc catacttggc tttaatattg tgggatagca acaatatcc acaacactga    840 tgataactaa actacaaatc tgacgttact tcagactact cacgtgtcaa aagcagttag    900
cgaggatcaa gtcttttagt ctggtcatta acaaacgcaa tttcgcaacc cgataatccg    960
cgatgataat atagcgactc caaggtcgta tttatattca atcaattccc cccaatttgg   1020
aatggatttt tggaatcatc gcatgccagg acaatcagtg aaacagtgac aaagtgaagc   1080
```

| | |
|---|---|
| ttcttgatca tttagcaact | 1100 |

<210> SEQ ID NO 34
<211> LENGTH: 78
<212> TYPE: DNA
<213> ORGANISM: Talaromyces cellulolyticus

<400> SEQUENCE: 34

| | |
|---|---|
| atgtctgcct tgaactcttt caatatgtac aagagcgccc tcatcttggg ctccttgctg | 60 |
| gcaacagctg gtgctcag | 78 |

<210> SEQ ID NO 35
<211> LENGTH: 1827
<212> TYPE: DNA
<213> ORGANISM: Homo sapiens

<400> SEQUENCE: 35

| | |
|---|---|
| aagtgggtca ccttcatctc tctcctcttc ttgttctcca gcgcctacag ccgtggtgtt | 60 |
| ttccgtcgtg acgcacacaa gtccgaagtg gcccatcgct tcaaagacct cggtgaggaa | 120 |
| aacttcaagg ctctcgtctt gattgccttc gctcagtact gcaacagtg ccctttcgag | 180 |
| gaccacgtga agctggtcaa cgaagttacc gaattcgcca aaacctgcgt tgctgacgag | 240 |
| tctgccgaaa actgcgataa gtctctgcat accttgttcg cgacaagct ctgtactgtc | 300 |
| gctaccctcc gtgagaccta cggagaaatg gccgattgtt gcgccaagca ggagcctgag | 360 |
| cgtaatgagt gctttctgca gcacaaggac gacaaccca atttgcctcg gcttgttcgt | 420 |
| cctgaggttg acgtcatgtg taccgccttc cacgataacg aggaaacctt cctcaagaag | 480 |
| tacctctacg agatcgcaag acgccatccc tacttctacg ctcctgaatt gctgttcttt | 540 |
| gccaagcgtt acaaggcagc attcactgag tgttgtcaag ccgctgacaa ggccgcctgc | 600 |
| ttgctcccca gttggatga actccgcgat gagggtaagg cctctagcgc caaacagcgc | 660 |
| cttaagtgcg cctcttttgca gaagttcggt gagagagcct tcaaagcctg gctgttgct | 720 |
| cgtctatccc aacgtttccc taaagccgag tttgctgaag tttccaaaact cgtcactgac | 780 |
| ctgacaaagg tccatactga gtgctgccac ggtgacttgt tggagtgtgc tgatgatcgt | 840 |
| gccgatttgg caaagtacat ctgcgagaac caggacagca tctcctccaa gttgaaggag | 900 |
| tgctgcgaaa agcccttgct cgagaagtcc cactgcattg cggaggtcga aacgacgaa | 960 |
| atgcctgccg acttgccttc tttggctgct gacttcgtcg aaagcaagga tgtctgcaag | 1020 |
| aactacgctg aagccaaaga cgtgttcttg ggcatgttct tgtacgagta tgctcgtcgc | 1080 |
| caccctgact actccgtggt tcttctcctc cgtctcgcca agacatacga cgactttg | 1140 |
| gagaagtgct gtgccgctgc cgaccctcac gagtgctatg ccaaggtctt cgacgaattc | 1200 |
| aagcccttag tcgaagaacc tcagaactta atcaagcaga ttgtgagct attcgagcaa | 1260 |
| ctcggtgagt acaagttcca gaacgcgtta ctggtccggt acaccaagaa ggttccccaa | 1320 |
| gtctccactc ctaccttggt tgaggtctct cgtaacttgg gtaaggttgg aagcaagtgc | 1380 |
| tgtaagcacc ccgaagccaa gcgtatgcct tgcgctgaag actacctgtc ggtcgtcttg | 1440 |
| aaccaattgt gcgtcttgca cgagaagact cccgttagcg atcgtgttac caagtgttgt | 1500 |
| accgaaagct tggttaaccg tcgtccctgc ttctccgctt tggaagtcga tgagacttac | 1560 |
| gttcctaagg agttcaacgc cgaaaccttc accttcacg ctgatatctg cactctgtca | 1620 |
| gagaaagagc gtcagatcaa gaagcaaacc gcactcgttg agcttgtcaa gcacaaaccc | 1680 |

| | |
|---|---|
| aaagccacca aggaacagct caaagccgtc atggacgatt tcgctgcctt cgtcgagaaa | 1740 |
| tgctgcaaag ccgacgacaa ggagacgtgc ttcgcggaag agggcaagaa gttggtcgcc | 1800 |
| gctagtcaag ctgctcttgg tttgtag | 1827 |

<210> SEQ ID NO 36
<211> LENGTH: 497
<212> TYPE: DNA
<213> ORGANISM: Talaromyces cellulolyticus

<400> SEQUENCE: 36

| | |
|---|---|
| atcagctttg agtgcagcaa aaatgcttcc gactgtcttc ttatattgat atcatatttt | 60 |
| tcaattcact ttgtctcaag tttcaatata tcgagaaaat agtatcaaag atgaactgta | 120 |
| ataattccga tacctata caggtttata gtaaattact ctatttcata atgcgtccat | 180 |
| ccgagaagtc tggcggcctt atcagtagtc caaaacgcct ggttttaga catgtcacct | 240 |
| ctaatctccg cttgaggaaa atgcgtccga gcaagttctt tcgacggggt gtcttgggtc | 300 |
| gtagttggag atatgatatt tattacttcg aatcctttga tattctcact cttttcaacc | 360 |
| gccaaaaggc aagctcttgc cactgcgcga ggattaaccc atccccagag ttgtcgaacc | 420 |
| ccagattcat accatttatc gtggtgtctt tttctaacat ctctcaatgg ggcaacctca | 480 |
| tgtattctca aacaagc | 497 |

<210> SEQ ID NO 37
<211> LENGTH: 2858
<212> TYPE: DNA
<213> ORGANISM: Talaromyces cellulolyticus

<400> SEQUENCE: 37

| | |
|---|---|
| gtcaattcag atcggctgcc gcctgcgccc caggtgacgt cgatgaaagc tgggcctagg | 60 |
| tcgtgcatgc ggtccatacg gtcgtataag ttctggacac cttgggcggt ctttgggggg | 120 |
| aagtattcga aggaaattcc aggtcggccg gtggccgcct gttcttggag cttttgcccg | 180 |
| acatgcatgt tgataggtcg gtcaattgtc tgcttttca atatcttctc ggtatgatgt | 240 |
| agcttgcaga acccaagtta tgtagttcaa ttgcaaaatc aagtctgatc aagaccgaaa | 300 |
| ctcaatcccg gagcactgag gttcgcacta attgatcaag ggtacaagaa tgagggcac | 360 |
| aatgaaagca gtcttgaaaa tgacaggcag agaaattgaa agaaaggaga gagaggacc | 420 |
| tccgggacag gagaaatgaa agcaacaaaa ccccgaacaa gctggagaga gttaaaggg | 480 |
| agcagcttgg tcaccggcaa tggatgctca tcataaaaaa ggaccctaaa cccgttatcg | 540 |
| gagtccggag aaatgacgct aattcggatt tggaagtccc cgccaatcgt gggaaattct | 600 |
| cgaagcagac aatttgctcg tgacaatcag ccagcaatga gagggagact gaaaaatatg | 660 |
| tatttacact caaagaatcc gatactgcta ttaggatcag tgttttctt ataagcaaat | 720 |
| gagcgttgga cgtggaaaat gaggaatcct cagtccctat actcggtcag cgacggaggg | 780 |
| gtgcgtgatc ggccaatcac agcctattat tttatcaaca tctgattggc tacttccgat | 840 |
| aagagcgaaa tatgcccctc cttgcaattt ttaccatcaa cgctaacagc aacactcaac | 900 |
| aaaccattca atcttgatac tcgctcccat tagtcaccac gcaggacaac acaacacgac | 960 |
| atcgcatctc agctttgacc attcccgccg caagcgattc gctgtcacaa cgccagata | 1020 |
| ccccaacatg gctgccctc cctccgccga tcaggactac aagaccaatc tgttgtcttt | 1080 |
| gctgatagcc aacgatgcgc tcgcattggg cacgttcaca ttgaaatctg gtcgccagtc | 1140 |
| gccgtatttt ttgacctcga gtcgtctta tactgcgcct ctgctgcgcc aggtgtcggc | 1200 |

```
cgcgttcgcg aataccatct cgtccccgcc ttttgtgaat atagctgcag atggcagcat    1260 tacccgaac  tttgacattg ttttgggta  tgttacccta ttattcgtgc gcctgatatg    1320
```

| | |
|---|---|
| cgcgttcgcg aataccatct cgtccccgcc ttttgtgaat atagctgcag atggcagcat | 1260 |
| taccccgaac tttgacattg tttttgggta tgttacccta ttattcgtgc gcctgatatg | 1320 |
| cgtgtactga tttacttcaa atagccccgc ctacaaagga atccccgaat gcgtcggtgt | 1380 |
| tgtcaacgag ctcgctaccc gggatgcgct cgccggtacc aagacatggg acaacatcag | 1440 |
| ctactccttc aaccgcaaag aagccaaaga ccacggcgaa gggggtaaca tcgtcggtgc | 1500 |
| gcctctcaag ggaaaacgtg ttttgatcgt tgacgacgtc atcaccgctg gtaccgcgct | 1560 |
| gcgtgaagct gtcggcatta ttcaaaagga aggcggaacc gttgccggtg ttgtgttgct | 1620 |
| gttcgatcgt caggaacggg tcagtgatac ggagcagaag agtgccattg agccgcgga | 1680 |
| gagggacctt ggaggcgata ttcctatccg tgcggtgttg gtattccagg atttgattga | 1740 |
| taagcttgga gataagattg gtcaggagga ggtgcgcagg ttggaagagt accggaacac | 1800 |
| gtacaaggct caataaatgg ctgctgtggg atgaaatggg tatattaacg atttatgcta | 1860 |
| aaaatggctg ggtggaatac tgcgaaataa atataaatca gcttgaagga tgtattttta | 1920 |
| gcgcaaagtg atagaatttt ctatgtaaat agtttgtaca ataggattac tactttatat | 1980 |
| gcgttatgcg tatacatttc taaagtgtaa ccagtttagc tgggagtaca atttaacac   | 2040 |
| tcttccatca atcaggttcc agatcagttt tctatctaca atcatgactc cccagtctct | 2100 |
| actcctttca agaatgacgc gttatgttcc aagctcccct ggttgatggc ggtaacccga | 2160 |
| tatattctag ccaggtcagg tcctagtgtg aggactaaca caggcacgtc cagtatcgta | 2220 |
| gcaaatagaa tatcagcata taagtcccc  ctttcccgga ccttgctcga gtcagtgact | 2280 |
| agcaggtacg tacgtaccca tcagactatc tactatctac tatgtacgga gtatatagtc | 2340 |
| ggtacttgac gcaaggcgag tctgatagag ggacaatatg cagttctgta gccaatcaat | 2400 |
| cgcggatggc agaccctcga tcgtcattgt ggatctttag cttccttatg ggcggggcgg | 2460 |
| tggttatttc agagccattt agccaatcat acatcgtagt ccgaaagtct aggattatat | 2520 |
| aggctagacc aatctactgt caaccggtaa agcgggtctc tagtctttat cccgacctcc | 2580 |
| tctctttctc tttctccgat tcgaatgtga cacatacatc tgatcaattg ataagaatac | 2640 |
| ggattgccgt gtacgtgggc tgacagagct gagataaaat atcctggatg tgatatgtgg | 2700 |
| cgcatccagt accgacactg tgacaggatc cgtgtactac aattcattca tcgatcgttg | 2760 |
| gctaggcaaa aagtaggcaa ggtttgcaga tcgatatccc ggtacctggc taaaatcgag | 2820 |
| acccatctac atatagtact gactcggcgt tcacttat | 2858 |

<210> SEQ ID NO 38
<211> LENGTH: 1356
<212> TYPE: DNA
<213> ORGANISM: Homo sapiens

<400> SEQUENCE: 38

| | |
|---|---|
| gaagtccagc tcgtcgagtc tggtggtggc ttggtccaac ccggtggatc cttacgtctc | 60 |
| tcttgtgcag ctagcggttt caacatcaag gacacctaca tccattgggt tcgtcaagct | 120 |
| cctggcaaag gtttggaatg ggttgcgcgt atctacccta cgaacggtta cacccgttat | 180 |
| gccgacagcg ttaagggccg tttcaccatt tctgccgaca cttccaagaa caccgcctac | 240 |
| ttgcagatga actccttgag agccgaggat actgccgtct actactgcag ccgttgggga | 300 |
| ggtgatgggt tctacgccat ggactactgg ggtcaaggca cccttgttac cgttagctcc | 360 |
| gccagcacaa agggtcccctc cgtcttccct ttggctccct cctccaagtc tacttccggt | 420 |

| | |
|---|---|
| ggtaccgctg cactgggttg cttggtcaag gactacttcc ctgagcccgt cactgtcagc | 480 |
| tggaattctg gcgcattgac ttctggtgtc cacacttttc ccgctgttct ccaatcttcc | 540 |
| ggcttgtaca gcctaagcag cgttgtcact gtgccctctt cctccttggg cactcagacc | 600 |
| tacatctgca acgtcaacca caagccctcc aacacgaagg ttgacaagaa ggtggaacct | 660 |
| cccaagtcct gcgataagac ccacacctgt cctccctgtc ctgctcctga actgttgggt | 720 |
| ggaccctcag tgttcttgtt ccctcccaag cccaaggaca ctctcatgat cagccgtact | 780 |
| cctgaggtta catgcgtcgt cgtcgatgtc tcccatgagg atcctgaggt caagttcaac | 840 |
| tggtacgtcg acggtgtcga ggtccacaat gccaagacca gcctcgtga agaacagtac | 900 |
| aactccacct accgcgttgt ttcagtcttg accgtgttgc accaggattg gctgaacggc | 960 |
| aaggagtaca agtgcaaggt ctccaacaag gccctgcctg ctcccatcga gaaaaccatc | 1020 |
| agtaaggcca aggtcaacc tcgcgaaccc caggtttaca ccctccctcc ttctcgggac | 1080 |
| gaactcacca agaaccaggt ctcgttgact tgccttgtta agggattcta ccctagcgat | 1140 |
| attgccgttg agtgggagtc caatggtcag cccgagaaca actacaagac tacccctcct | 1200 |
| gttctcgact ctgacggatc tttcttcctc tacagcaagt tgaccgtcga caaaagccgt | 1260 |
| tggcagcaag gcaacgtttt ctcctgctct gtcatgcacg aggctctcca caaccactac | 1320 |
| acacagaagt ctctgtcctt gtctcctggt aaataa | 1356 |

<210> SEQ ID NO 39
<211> LENGTH: 1680
<212> TYPE: DNA
<213> ORGANISM: Talaromyces cellulolyticus

<400> SEQUENCE: 39

| | |
|---|---|
| attttcactt ctttcttcgc ctattgattg ggctatgaca aaattaggag agataggttg | 60 |
| gacgttgtca agtcaaaatg taccgaacac gatgcgttga tatgctgcac atgtgcctag | 120 |
| tatccattcg ttcctattta tattaaattg aaatttctct atccaattac tgagctaaaa | 180 |
| catacttcag cactgtaagc gccagcctaa gttatgctat gttagactgt ccggattcgg | 240 |
| ctggcactgg cttttgtgat ccccagtatc atgtaaaggt atccgcctgt ttgttagggg | 300 |
| gtcttaaatg ttgtataaag tttcttgcta ggctgtttat gcttgataga gaatatatat | 360 |
| atatatctag ctgctattaa tatccttgtt tcaatgtctt agacttccaa ggttacctac | 420 |
| ccgcgtgcgt ggactaatac aaacaatctc actcaagaca atcttataca aactcggatt | 480 |
| ctggtcaatc cgttccttgg ttatattgct aaaaaaacta ggtagcccaa aattccatct | 540 |
| caagccgtat aagaactttc aaattcacca tggtactctc acgggcgaag catctccgtc | 600 |
| ttccatctgc caaaatccat taccaaaatc ggaagtaccc gaatgtagca atgaacaat | 660 |
| aactttcgca ccatctagcg gatcctttgt gccacgatag ttgttgaacg cagttttgca | 720 |
| atacccagga ctaactgctt ggatgataac actctcattc gccgggtctt tcccatattc | 780 |
| gaccgtgagc atgttaaggg ccgtctttga ggcgcagtac gcgatagtaa cagttggagg | 840 |
| cagcttgcca gatgatgata ggcccaaaga accccgtgtg gatgatacgt ttattatgtg | 900 |
| gcctcgaggc gactgacgca aaagtggtag gaatagatct atggtcattg cgaccgatgt | 960 |
| gacattcaca tcaaaagttc ggttgtaagt agaccgcatt tcggaaaatg aagtctgggt | 1020 |
| gaaggcaacg gcagcattgt ttatcagaac tagacatctg ttagagaatt tctaaagccc | 1080 |
| gctcactcga gaatgaaata ggcttaccat ccagtctacc atatgttgtc tcgaccgcct | 1140 |
| tagcaaaagc aatgaggcta tcgtcgcgag tcacatcaac ctccataacg tcgatcttgg | 1200 |

```
attgaacagc gagctctctc aaccgcttaa gtgcctgatt tccgtcttcc ttattccggc   1260
atcctaagat gaagtgatcg gatggactat gcagacttaa agcctggagg gtaccaaacc   1320
cgatgcctga caattattag tgatcatata gaatgagtat catggccatc gcaaatctac   1380
ctctgtttgc tccagttata agaattagcc ttgatgacat cttgtgagag aagtaaaaga   1440
taatagcaga tgaatttcga tcgtatactg gttgtattgg caatcttgac gagaatggtt   1500
tcattgtcag accatcagtt cccttatat acctgccatt ctctccttta taaataatta   1560
ttcggtttta acacggagat actcggattt catcacacaa attgcatttc ttccgatagt   1620
tgttgaagat cggaagtcct tcgaatgatc atttctataa ctacgcctta ccgttttcgg   1680
```

<210> SEQ ID NO 40
<211> LENGTH: 645
<212> TYPE: DNA
<213> ORGANISM: Homo sapiens
<400> SEQUENCE: 40

```
gacatccaga tgacacagtc cccttctagc ctttctgcct ctgttggaga tcgtgtcacc   60
atcacttgtc gtgcttctca agacgtcaac acagccgttg cctggtatca gcagaaaccc   120
ggcaaagctc ccaagttgct gatctacagc gctagcttcc tgtacagcgg tgtcccttct   180
cgcttctcag gttcccgttc tggtaccgac ttcaccttga ccatttccag cttgcaaccc   240
gaggatttcg ccacgtacta ctgccagcaa cactacacca ctcctcccac ctttggccaa   300
ggtaccaagg tcgagatcaa gcggactgtt gccgcacctt ccgtcttcat cttccctccc   360
tcggatgagc agctcaagtc tggaactgcg tctgtcgttt gcttgctcaa caacttctac   420
cctcgtgaag ccaaggtcca gtggaaggtc gacaacgctt gcagtccgg caatagccaa   480 gagtccgtta ccgaacagga cagcaaggac tccacttact ccttgagttc cactctcacc   540
ttgtccaagg ccgattacga gaagcacaag gtctacgctt gcgaagtgac ccatcaaggt   600
ctctctagcc ctgttactaa gtccttcaac cgtggtgagt gttag                  645
```

<210> SEQ ID NO 41
<211> LENGTH: 1354
<212> TYPE: DNA
<213> ORGANISM: Talaromyces cellulolyticus
<400> SEQUENCE: 41

```
ctcgtgaaag ctgccctcac aatgatcgtc aagatgacgt agtttgactg ggtcgttcct   60
ggataagggt tagggtaaat agggctcaaa gtaccacgtg agtgtggaaa gataagccct   120
aaccctaagg tcgtgtcgga caaaaattat cacttgacca aaattggaga tccccttaat   180
ggagcttttt ggtaatggtt tgtatagggt tatgtgacgt ccgtatcaca tgattttat   240 cccaacaggt cgatcccct cttatagtta atggacaaca tataagtacg tagcatctta   300
gatagttcgt cagcgtcaac tgaccaaagt ccccgtgttt cattttaatt tgtcagactg   360
caagagtctc gaaacataaa aagatcgaaa gttttgcctt attaggctat gagcatgaat   420
gtcggaacaa tgccgttgag gctattccca atttcggaaa tatgtatctt cattgctgtc   480
gacttgacga cagtcgataa aaggctcatc cggatagata agccagatca ctcattatgc   540
caatttctcc ggtgtctgaa aacgtatact acatacgtaa ctgatcttcg tggttgaaag   600
agtgtttctt ctcattctca tctgccgatg ccgagccaat tggaacaaac ccgcatatg   660 gtcctgaata tcaatcgcgg agatgcggag agtgagggag caacacaatt ttaaattagt   720
```

| | | |
|---|---|---|
| cagtttctc atgttctccg caatcttgca ggcttgggtc tggtaggttt atctctctct | 780 |
| tttcacaaca aggttgggcc attgtcagct tagcaagcgc gcagcaaagg gtgtcggtca | 840 |
| atgttcatgt cctccgcggt cactacaaaa cagcacgtgg ggaatgttgc tttccctgtt | 900 |
| gatgttcatg tgttgtcatt cccggcaaat cgactccaat taatatggta ggctcctgca | 960 |
| taatgcaagt ccttgagatg cagcttccgg cagatggacg tatagatcag ggactttgag | 1020 |
| gggctaaaac acttacccga gctaaaacat accataattt cgtttaatga ctttcgtctg | 1080 |
| gatggcagag gctgaaggtc gattatgagt gaaattggta tgaagccaca tacgccgata | 1140 |
| ctgtaacgct gtgccttcat ccgccttcta tcgcgcccg acattccgcg gtaccgcgat | 1200 |
| tatgaagaaa acactcgta atgatgagga gatagttctt agctcttatt atttttgtct | 1260 |
| agctatggaa tgcaagttta gcactatata atggtggtgt ttcccttgaa gaattaggca | 1320 |
| ctatcaaccg caacagtcag aagcaatcga caca | 1354 |

<210> SEQ ID NO 42
<211> LENGTH: 26
<212> TYPE: PRT
<213> ORGANISM: Talaromyces cellulolyticus

<400> SEQUENCE: 42

Met Ser Ala Leu Asn Ser Phe Asn Met Tyr Lys Ser Ala Leu Ile Leu
1               5                   10                  15
Gly Ser Leu Leu Ala Thr Ala Gly Ala Gln
            20                  25

<210> SEQ ID NO 43
<211> LENGTH: 490
<212> TYPE: PRT
<213> ORGANISM: Talaromyces cellulolyticus

<400> SEQUENCE: 43

Met Lys Gly Val Leu Ser Leu Ser Leu Leu Pro Leu Leu Thr Val Ala
1               5                   10                  15
Ser Pro Val Met Pro Arg Thr Ile His Asn Asp Ala Ala Pro Ile Leu
            20                  25                  30
Ser Ser Ser Asn Ala Val Glu Val Pro Asp Ser Tyr Ile Ile Val Phe
        35                  40                  45
Lys Asp His Val Asp Ser Ala Ser Ala Ala His His Asn Trp Val
    50                  55                  60
Gln Asp Ile His Ser Gln His Thr Glu Leu Arg Lys Arg Ser Gln Phe
65                  70                  75                  80
Pro Phe Ala Asp Asn Ala Phe Ala Gly Leu Lys His Thr Phe Asp Ile
                85                  90                  95
Ala Gly Ser Phe Leu Gly Tyr Ser Gly His Phe Glu Glu Asn Val Ile
            100                 105                 110
Glu Ala Ile Arg Arg His Pro Asp Val Asp Tyr Ile Glu Lys Asp Ser
        115                 120                 125
Leu Val His Thr Met Glu Asp Pro Ala Leu Glu Lys Asn Ala Pro Trp
    130                 135                 140
Gly Leu Ala Arg Ile Ser His Arg Glu Ser Leu Ser Phe Gly Ser Phe
145                 150                 155                 160
Asn Lys Tyr Leu Tyr Ala Ala Asp Gly Gly Glu Gly Val Asp Val Tyr
                165                 170                 175
Val Ile Asp Thr Gly Thr Asn Ile Asp His Val Asp Phe Glu Gly Arg
            180                 185                 190

```
Ala Ser Trp Gly Lys Thr Ile Pro Thr Asp Asp Glu Asp Val Asp Gly
            195                 200                 205

Asn Gly His Gly Thr His Cys Ser Gly Thr Ile Ala Gly Lys Lys Tyr
        210                 215                 220

Gly Val Ala Lys Lys Ala Asn Val Tyr Ala Val Lys Val Leu Lys Ser
225                 230                 235                 240

Asn Gly Ser Gly Thr Met Ser Asp Val Val Gln Gly Val Glu Trp Ala
            245                 250                 255

Ala Thr Gln His Ile Lys Lys Val Lys Asp Ala Lys Ala Gly Lys Ala
            260                 265                 270

Lys Gly Phe Lys Gly Ser Ala Ala Asn Met Ser Leu Gly Gly Gly Lys
        275                 280                 285

Ser Val Thr Leu Asp Lys Ala Val Asn Ala Ala Val Asp Ala Gly Ile
        290                 295                 300

His Phe Ala Val Ala Ala Gly Asn Asp Asn Ala Asp Ser Cys Asn Tyr
305                 310                 315                 320

Ser Pro Ala Ala Ala Glu Lys Ala Val Thr Val Gly Ala Ser Thr Leu
            325                 330                 335

Ala Asp Glu Arg Ala Tyr Phe Ser Asn Tyr Gly Lys Cys Asn Asp Ile
            340                 345                 350

Phe Ala Pro Gly Leu Asn Ile Leu Ser Thr Trp Ile Gly Ser Lys Tyr
        355                 360                 365

Ala Val Asn Thr Ile Ser Gly Thr Ser Met Ala Ser Pro His Ile Ala
        370                 375                 380

Gly Leu Leu Ala Tyr Phe Leu Ser Leu Gln Pro Ala Ser Asp Ser Ala
385                 390                 395                 400

Phe Ala Val Ala Glu Ile Thr Pro Lys Lys Leu Lys Glu Asn Leu Ile
            405                 410                 415

Ala Ile Gly Thr Gln Gly Ala Leu Thr Asp Val Pro Ser Asp Thr Thr
            420                 425                 430

Asn Ile Leu Ala Trp Asn Gly Gly Ser Ala Asn Tyr Thr Asp Ile
        435                 440                 445

Ile Ala Gln Gly Gly Tyr Lys Thr Lys Thr Leu Ser Asn Glu Val Asp
        450                 455                 460

Glu Leu Ile Asn Lys Leu Glu Val Val Asn Glu Glu Leu Gly Ala Ile
465                 470                 475                 480

Tyr Ser His Ile Lys Asp Ala Ile Ala Ala
            485                 490

<210> SEQ ID NO 44
<211> LENGTH: 4509
<212> TYPE: DNA
<213> ORGANISM: Talaromyces cellulolyticus

<400> SEQUENCE: 44
atgtcgagaa gaatacggaa ccctgattcc gcaggctcga gtcaaaccct aagtaattca      60
ccggtaccaa tagccgccga atccggcacg gaacctgtgt acctaggtcc gtatcgaata     120
gcgaagtttt ccgtctattc ttcgaatttt gtatacatgc ttaccttggc tcaaaggtac     180
tcacaaagtc cgaagaataa attatagaac cgatgtgaaa cggggacagt ttggcaaccc     240
cttgtactat gtacattgta tggatctcgt ctcgactctc gagacgaggg tttcgtacca     300
accaaagact caaacttggg gtaactaagc gatcggctg cgtagtactc catactccat      360
aaataccccg gtgaattcgc ctcttgccca tggaatgagc gagaatttac ccttggagtc     420
```

```
atcgcggtaa atgactcaca tatcatgtct gccttcactc tcctcaacct ttgaaattcc    480
ggttaatgtt aaggcgaggt gtcctctacg gaatggcttt gtagatttga gataagacta    540
cgccgtaact taagggatcc acatactcca tattgatagt ctcaggaccg agatagtctg    600
gagtaacccc gtacccaatc aacgtcctca gactcgccac ctggttacaa tatttcggtg    660
cttgtgccga tatacctccg ttgcgtgagc cttgatagcc aacaagaaat gattcaaaat    720
taagatttga gaaaatccgg agtacgcagt gcctgcagtg taaaaaataa tgtatttacc    780
taatgccaat atgtcgatgc caaagtacta ctagcaaaga cactagatat gcagcaaact    840
cgatgtttag gtacatgtaa ccatatcctg gggtcaggta cgaacgccat caattaatct    900
cgtaaactag ctgtcacacg acagtatcat ttgatagttc aatgttcca tgctccccct     960 caaatgtcac tggatgatac gaatttggct gtgacttgaa cagatagacg gaaaacagtc   1020
cgatcattat ccggagtacg catgtacgag atagtctggg gatcctcggc tgccccgatt   1080
ggggttagtg cgggttttcct tatcttgata cgccgtctgg aggcgcaggt gattgttacg   1140
gtgtgttccg tgatagataa gttagacatc cgataataac ctatcttcta gatagacggc   1200
aggtacgtat gtagatagat agatgacaca gtcataagac agtttttattt accatacata   1260 gtatagtcat ttgacaaaca cttgatgact atgagcagta agtccagaca agagcataga   1320
ctagaaatga tgtgatcatc aataggtacg gagtcgtacc accccggat tatcttggct    1380 ggcttagtca cgcccaaaca gacggtgacg gatgagacac aagcaaagag cgacattccg   1440
aagaattctc gtgacggaaa cgagaatgcc gccggcgctg ataggggaa attttatctt    1500 ttcccttttct gacattcagt gtttacaata caatacggaa ttacggaacc ccggttttcg   1560
caaccggtgg aattacctaa tgggtgacct gaatttatta gataacgatg aacaatttgt   1620
tggatcttcc gtagatcgat ttggacttga taggtgcttc caaggttgtt gctgctcaca   1680
tggtcgcttg cgttatctgc ctacagaatg aggaagatgt attccgcacg tactccggtc   1740
gcgacagata tgcgacgatt gcaatatgta ctacatagtt agtacataca actctagact   1800
agactctata ttatgtagag tgtaagagaa aagaaagaa gataacggca gggtctattt     1860
gattgcgcta taatatgcgc cgctgtatgg ttccccagat ctgcgtgaga tatcacctca   1920
tcctatcatc attccaggtc aaagtctcgt catcatgaat tggtattatt acccagtacg   1980
taaaccacgt atcgaggcgt atcggtgtat taaagataga gctactgcat ggctctagt    2040 cctatctttg ccccggaatc cggcccgtgg atgacgatat gatgctgttt gtccttcagc   2100
taaacacgga cgatctctta cagggtgcgg ttaattatta aggatataat tctaatcaac   2160
gactctggct gtgctatatt aacaatgtct tctaagtggt catgatgtgt acgtacttcg   2220
tacacatgct acatgcaatc gagtacgtaa ctccagatct cgccgtacc cgcgataccc    2280 gggccatcat gcaaatgtaa ccgcttggaa cacgcactgc agtgcataaa agccacagcc   2340
tcgcttccca atccggttta gacgcgtttt gtcttgctgt tttgggagca gccagacccc   2400
acattccact aacccactct ttttcagcgc ttattctcgt aagattcgta cgaaaaatac   2460
atctgcccac actatccacc agctcggcca ctcttcggtg agaacgctgc catgagaaaa   2520
aaatctgcga ctctgcaaca gagtgaggca cggctgaacc gagctgattg tcaccctttg   2580
cccaatgccc agacagccca gacagcccag acagcccaga cagcccagac agcccagaca   2640
gcccagacag ccagtgcttg gttaattttt actaagggta aaaacctaaa aaaagaaac    2700 gaaaaaaaaa aaaaaaaact tttcttttttt gcccccaat cacttggccg acagtcaaag   2760
```

```
ggttccccca cacggtactc cgtacttgct acgtacacta actaaagaaa aaatctcctg    2820
attgagtctg tgtctgtctg tcgctgctaa actcggataa ccccccgttc ccgatcaccc    2880
gtcgaaaaga gcagcagcca tttaacattt ttcccctcca ttcctccttc ttggaacttt    2940
ccctccctcc ctcatcctta catctccctg cgtgcgcgcc tgcctgccta cttacactgc    3000
cactccccag atttttcttc tcttgtttct tctccagact ttctttcctc ctccacctcg    3060
cctcaccaca ccaccaccac cactcaccac gccaacaaca ccgcactacc actactgctt    3120
caaagatcga tcaggccatt atcaaggagg atcgacgtct tattccatcg accaccctgt    3180
tgatcacctc ggctggagcg ctcgactccc tggcttcctt ccccagctta tttaaacccg    3240
tcacccgcca ggtctcttca catgtcaccg tcatcttcgt cagtgggttt ttccaatctg    3300
ctgaacccac agtcagactc tgtcgagcct acggataaca catcttcacc tgctaccacc    3360
actaccaccg gcacagactc caactcagac aaggaaatgg cgtcctctgt cagtctgctc    3420
ccaccactca tgaagggtgc ccgcccgcc gcggaggaag tgcgacagga cctccctcgt    3480
ccatacaagt gtcctctttg cgatcgtgct ttccatcgtc tagagcacca aactcgtcac    3540
attcgtactc acaccggcga gaaacccat gcctgccagt ttccaggctg cacgaaacgg    3600
ttcagtcgtt cagatgaatt gactcgtcac tcgcgcattc acaacaaccc caactcgaga    3660
agaagtaaca aagctcagca tattgctgcg gctgcggcgg ccggtcagga ttcgggtatg    3720
cttaacgctg ctgcctcgat gatgcctcct ccaagcaaac ccattactcg ctcggctcca    3780
gtgtctcagg tcggatctcc ggatgtgtct cctccgcact cttacaccaa ctacacctcg    3840
catttgcggg cgggtctggg tccttattca cgcaacagcg accgtgcttc atctggtatg    3900
gatattaatt tgctcgcgac tgctgcttca caagtcgagc gcgatcacta cggaggctcg    3960
tctcgtcatt ccctttcag ctctcgatac tcgggtactc ctggacgtct accgtcgctt    4020
tccgcctatg ccatttctca gagcatgagc cggtcgcatt ctcacgagga tgaggacaac    4080 tacgacatc accgggttaa gcgctctcgt cctaactcac caaactcgac tgcgccatcc    4140
tcgcctacat tctctcacga ttcattgtcg cctacccccg atcacactcc tcttgcaacc    4200
ccagcacact cgcctcgttt gcgtccttat ggagccgcag atttgcaatt accttccatc    4260
cgtcatttgt cgttacacca cactcccgca ctcgcaccaa tggagcctca agccgaggga    4320
cctaatgttt acaaccccgg tcagcaccac ggtggaccca gcatcacgga catcatgagc    4380
aggcccgacg gcacccagcg taagcttcct gttccgcaag tacccaaaat cccggtgcag    4440
gacatgttgg caccgaacgg atattcctcc aacactccgt ccgtcaacgg ttccgtgatg    4500
gagttataa                                                           4509
```

<210> SEQ ID NO 45
<211> LENGTH: 1323
<212> TYPE: DNA
<213> ORGANISM: Homo sapiens

<400> SEQUENCE: 45

```
caggttcagc tcgttgaaag cggtggtggt gtcgttcaac ccggtcgttc cttgcgtctg      60
gactgcaagg ctagcggtat caccttctct aactctggta tgcattgggt ccgtcaagcc     120
cctggtaagg gccttgagtg ggttgccgtc atttggtacg atggctccaa acgctactat     180
gccgatagcg ttaaaggtcg tttcactatc agccgtgaca actctaagaa cacccttttc     240
ctccagatga actctttgcg tgccgaggat actgcagtct actactgcgc cactaacgac     300
gactactggg gtcagggtac actcgttacg gtcagctctg ccagtacgaa gggtccctcc     360
```

```
gtctttccct tggctccctg ttcccgctca acctccgaga gcactgcggc tttgggttgc    420
ttggtgaagg actactttcc cgaacctgtg accgtttcct ggaattccgg tgctttgacc    480
tctggtgtcc cactttccct tgctgttttg cagtctagcg gactctacag cttgtccagc    540
gtcgtcaccg ttccttcctc tagcttgggg accaagacct acacctgcaa cgtcgaccac    600
aagccttcca acacaaaggt tgacaaacgt gtcgagtcca agtacggacc tccttgtccc    660
ccttgtcccg cacctgagtt cttgggaggt ccttctgtgt tcctcttccc tcctaagccc    720
aaagacacct tgatgatctc tcggactcct gaggttactt gcgtcgtcgt tgacgtctct    780
caggaagatc ctgaggtcca gttcaattgg tacgttgatg gcgtcgaggt tcacaacgcc    840
aagactaaac cccgtgaaga gcagttcaac tccacctacc gtgtcgtctc agtcctcacc    900
gtcttgcacc aagactggtt gaacggcaag gagtacaagt gcaaggtcag caacaagggc    960 ttgcccttctt ccatcgaaaa gaccatcagc aaggctaagg gccaacctcg tgagccccag   1020
gtgtacactt tacctccctc tcaagaagag atgaccaaga accaggtttc cttgacctgc   1080
ctcgtcaagg gattctaccc ctctgatatt gccgtcgaat gggagtccaa tggccaaccc   1140
gagaacaact acaagacaac tcccctgtt ctggactccg atggtagctt cttcctctac    1200
tcgagactga ccgtcgacaa gtcccgttgg caggaaggca acgttttctc ctgctccgtc   1260
atgcacgaag ccctgcataa ccactacacc caaaagagcc tatccttgtc tcttggtaag   1320
taa                                                                 1323

<210> SEQ ID NO 46
<211> LENGTH: 645
<212> TYPE: DNA
<213> ORGANISM: Homo sapiens

<400> SEQUENCE: 46
gaaatcgtcc tcactcagtc ccctgcaacc cttagcttgt ctcccggaga acgtgccact     60
ctcagctgtc gtgccagtca atccgtttcc agctacttgg cttggtacca gcagaaacct    120
ggtcaagcac ctcgtttgct catctacgat gcctccaatc gtgctacagg tattcccgct    180
cgtttctctg gctcaggtag cggtaccgac ttcaccttga ccatcagctc cttagagcct    240
gaggactttg ccgtctacta ctgccaacag tcctctaact ggcctcgcac tttcggtcaa    300
ggcacgaagg tcgagatcaa gcggactgtt gctgctcctt ccgtcttcat cttcccccc     360 tctgatgagc agctgaagtc cggaactgcg tctgtcgtct gtctgctcaa caacttctat    420
ccccgtgaag ccaaggttca gtggaaggtc gacaacgcct tgcagtctgg taactctcag    480
gagagcgtta ccgagcaaga ctccaaggat agcacctact ctttgtcctc cactttgacc    540
ctcagcaaag ccgactacga gaagcacaag gtctacgctt gcgaagttac ccaccaaggc    600
ttgtcttccc ctgtgaccaa gtcgttcaac cgtggtgaat gctag                    645

<210> SEQ ID NO 47
<211> LENGTH: 25
<212> TYPE: DNA
<213> ORGANISM: Artificial Sequence
<220> FEATURE:
<223> OTHER INFORMATION: primer

<400> SEQUENCE: 47
caggttcagc tcgttgaaag cggtg                                           25

<210> SEQ ID NO 48
```

<211> LENGTH: 37
<212> TYPE: DNA
<213> ORGANISM: Artificial Sequence
<220> FEATURE:
<223> OTHER INFORMATION: primer

<400> SEQUENCE: 48
agaagtgaaa atttacttac caagagacaa ggatagg                      37

<210> SEQ ID NO 49
<211> LENGTH: 25
<212> TYPE: DNA
<213> ORGANISM: Artificial Sequence
<220> FEATURE:
<223> OTHER INFORMATION: primer

<400> SEQUENCE: 49
gaaatcgtcc tcactcagtc ccctg                                   25

<210> SEQ ID NO 50
<211> LENGTH: 37
<212> TYPE: DNA
<213> ORGANISM: Artificial Sequence
<220> FEATURE:
<223> OTHER INFORMATION: primer

<400> SEQUENCE: 50
ctcaaagctg atctagcatt caccacggtt gaacgac                      37

<210> SEQ ID NO 51
<211> LENGTH: 507
<212> TYPE: DNA
<213> ORGANISM: Homo sapiens

<400> SEQUENCE: 51
tgcaacgaca tgacccctga gcaaatggct acgaatgtca actgttcctc tcctgaacgt      60 catcccgtt cctacgacta catggaaggt ggagatatcc gtgtgagacg tctgttctgt     120
cgcactcaat ggtacttgcg catcgataag cgtggcaaag tcaagggtac acaggagatg     180
aagaacaact acaacatcat ggaaatccgg actgttgcag tcggaatcgt tgccatcaag     240
ggtgtcgaaa gcgagttcta cttggccatg aacaaggaag gcaagttgta cgccaagaaa     300
gagtgcaacg aagactgcaa cttcaaggag ctcatcctcg agaaccacta caacacctat     360
gcttctgcga aatggaccca caatggtggt gagatgtttg tcgccttgaa ccagaagggt     420
attcccgttc gtggcaagaa gaccaagaag gagcagaaga ctgctcactt ccttcccatg     480
gccattaccc accaccatca ccatcac                                        507

<210> SEQ ID NO 52
<211> LENGTH: 40
<212> TYPE: DNA
<213> ORGANISM: Artificial Sequence
<220> FEATURE:
<223> OTHER INFORMATION: primer

<400> SEQUENCE: 52
acagctggtg ctcagtgcaa cgacatgacc cctgagcaaa                   40

<210> SEQ ID NO 53
<211> LENGTH: 40
<212> TYPE: DNA
<213> ORGANISM: Artificial Sequence
<220> FEATURE:
<223> OTHER INFORMATION: primer

<400> SEQUENCE: 53
ctcaaagctg atctagtgat ggtgatggtg gtgggtaatg                          40

<210> SEQ ID NO 54
<211> LENGTH: 513
<212> TYPE: DNA
<213> ORGANISM: Homo sapiens

<400> SEQUENCE: 54
gcccctatgg cagaaggagg tggtcagaat caccacgaag tggtcaagtt catggacgtc    60
taccaacgct cctactgcca tcccattgag acactcgtcg acatcttcca ggagtacccc   120
gatgagatcg agtacatctt caagcctagc tgcgttccct tgatgcgttg tggtggctgt   180
tgcaacgacg aaggcttgga gtgcgttcct actgaggagt ccaacatcac catgcagatc   240
atgcggatta agcctcatca gggtcaacac atcggcgaaa tgagctttct ccagcacaac   300
aagtgcgaat gtcgtcccaa gaaggacaga gctcgtcaag agaacccttg cggtccttgc   360
tctgaacgcc gtaagcacct gttcgtccaa gatccccaga cctgcaagtg ttcctgcaag   420
aacaccgatt ctcgctgtaa agcccgtcag ttggagctta cgagcgtac ttgccgttgc    480 gacaaacctc gtcgtcacca ccatcaccat cac                                513

<210> SEQ ID NO 55
<211> LENGTH: 40
<212> TYPE: DNA
<213> ORGANISM: Artificial Sequence
<220> FEATURE:
<223> OTHER INFORMATION: primer

<400> SEQUENCE: 55
acagctggtg ctcaggcccc tatggcagaa ggaggtggtc                          40

<210> SEQ ID NO 56
<211> LENGTH: 40
<212> TYPE: DNA
<213> ORGANISM: Artificial Sequence
<220> FEATURE:
<223> OTHER INFORMATION: primer

<400> SEQUENCE: 56
ctcaaagctg atctagtgat ggtgatggtg gtgacgacga                          40

<210> SEQ ID NO 57
<211> LENGTH: 1587
<212> TYPE: DNA
<213> ORGANISM: Talaromyces cellulolyticus

<400> SEQUENCE: 57
atgcgtatgt cagcttcgtt accgctcatc gtcttgtcga tggtgtcggc cagcaatgcg    60
ctctctcttc atagacgtga tgagccagca gttctagcag caccgttaca acgcagacat   120
gtggatggga ttttgggcaa aagagatacg tcgccagttg atgtatcgat cttcaatcac   180
gtacgtacga ggatttcgaa tgcaatattt cctgggacct aacgactgca tagcaaaata   240
caagctactg gctgaacttg actctgggat cacctgcgca gaatttcaca ctcgccttgg   300
acacgggcag cagcgatcta tgggttattg agggatcgaa aaaggcagct aatgtttacg   360
tctcggatga ttcgtcctct ttcaaatctc tggatcttcc atacaacgca acatacgcgg   420
atggcaccac ggctctcggt gtctacgcga ctgacatatt gagcttggga ggtgcaactg   480

```
tcaaggactt tgagtttatt gttgtgaacc aaacttcatc tgatggtgag atctgacctt     540
atgaaaatat cattgtatct tctgcaaact ttagtggcgt gtgcattcat tctaattcat     600
gattgattgt atacagtggg cattgccggt gtcggctaca acatctcaac atatgcatct     660
tcaggcctga acaaaacata caacaaccta ccttatgcct tggctgccag cggcgtcacc     720
aaatctgctg cttacagcct gtggatggac gatgccgcag caacttcagg cacgattatg     780
tttggtggtg tcaacaaggc aaagtacatc ggtgaactcc aaactctccc agtcgtgcca     840
gtctataaca ggtattactc acttgcactc gccttgaccg aagtcactgt gcaaactggg     900
gactccaaga gtactacgac gaaccttccg ctcgcagttt ctctggatac gggctcaact     960
tccactttgc tgccccaaga ccttttaat gacattctcg gcgctctgaa tggaacctac    1020
gacgagaaga gcggcttcgc ctatgtgagc tgcgacctca tagaaaccga ttacaatgtg    1080
acattcagtt tctctggagc taagatcgac gtgggtctta gtcaactggt attttttcggg   1140 gccgtggctg ggtggcccaa gaacagctgt gttattgatc ttactcccag cgaacctgga    1200
gtgaacatcc ttggagacag tttcctgcgc agtgcgtacg tcgtctatga ccttgagaac    1260
aatgaaattt cccttgccaa caccaacttc aaccccggta aggacgacat tctggaaatc    1320
ggtaccggcg ccgatggggt gccaggtgcc actcttgttc cctcggctgt ctctactgct    1380
acaggaaacg gcgttcagac agcgactacc ggtgtggtgg gtgctaccgg ggtcactgtc    1440
accgctggta ctactgctac cggcagcgca agcaccggcg ttctgcaaa atctactggc    1500 acatcttctg gcatggcagc gttgcccacc ggcaatgcca aacttctttc tggtctggca    1560
ggcgctggtc ttctccttat gatctaa                                          1587

<210> SEQ ID NO 58
<211> LENGTH: 2025
<212> TYPE: DNA
<213> ORGANISM: Talaromyces cellulolyticus

<400> SEQUENCE: 58
atggaactgt cccccgccggg cttagcgccg aacaggtatc gcatcaccat cggaccaagg     60
taactcccag tcgtgtggcc atccacccat ctgccccaac ttcatctctt catcttcatc    120
ttcatctcat tccggattcc cccagagagg tgtactgtat ctgggataca ctgttcaagg    180
ctttgtgtgc atcagacaca acaattatct tgtaagttgg ttcgtctctg actctccagc    240
tatcgttgag tcaccactga tactgataac gacgtcatct ccagattcga ctgctcgagc    300
catcaacatg aaaggtttgg ctaccacgct cctcgtaggg gctgcggctg ctttttctcc    360
tgctcagcag gtgcttaaag ccccagagga cgttgttgag aacacccaca aggcctcctc    420
tccctctcta gccgagacgc tcgcccagcc tctccatgag ctcaatgaag agctcaagtc    480
gttcactcac gaagccgagg aggtctggga acaagtctca aacatgttcc caggtgctct    540
agataacatc cctttcttct cctcacccaa gaagcacact cgtcgccctg actcacactg    600
ggaccacatc gttcgtggtg ccgacgtcca gaacatctgg gttgagaacg ccaatggcga    660
gaaggaacgt gaagtcggtg gtaggctcga ggcctttgac cttcgtgtca agtctgttga    720
ccccagctcg cttggaatcg atcccgatgt caagcagtac agtgggtacc ttgacgacaa    780
cgagaatgat aagcatttgt tttactgtat gtgcacactt ctatctatcg aaagtatcac    840
tgataactaa caattatagg gttctttgag tcccgaaatg accccaagac tgaccctgtc    900
gtcctctggt tgaacggtgg accaggatgc tcgtccttga ccggtctttt cttcgagctc    960
ggacccagct ctatcggcaa gaacatcaag cccatctaca cccctactc ctggaactcc   1020
```

```
aacgcctctg ttatcttcct tgaccagccc gtcaatgtcg gtttctccta cagcggtaac    1080
tccgtcagtg agacgagcgc tgctgcaaag gatgtctatg ctcttcttac tcttttcttc    1140
aagcaattcc ccgaatatgc cactcaggat ttccacattg caggtgaatc ctacgccggc    1200
cactacattc cttcatttgc ctctgagatc ctttctcaca agaagcgcaa catcaacctg    1260
aagtctgttt tgatcggaaa cggtcttact gatggtctca ctcagtacga atactaccgc    1320
cccatggctt gcggtgatgg tggttatcct gctgttctcg atgagagcac ttgccgctcc    1380
atggacaacg ctctcggtcg ctgccagtcc atgattcaat cctgctacga cagtgaaagt    1440
gcttggacct gtgttcctgc ttctatctac tgcaacaacg cccttttggg tccctaccag    1500
cgcactggcc agaatgtata tgatgtccgc aagccttgcg agggcggcaa cctctgctac    1560
actgatctcg aatacatcag cacctatctc aaccaggctg aggtcttgaa ggctgtcgga    1620
gccgaagttg acaacttcga ctcttgcaac tttgacatta accgcaactt cctttttcaag   1680 ggtgactgga tgaaaccatt ccacaagctt gtccctggaa tccttgagga atccctgtt    1740 ctcatctacg ctggtgacgc cgacttcatc tgcaactggc tgggcaacaa ggcctggtct    1800
gatgctcttg agtggagcgg ccacgaagaa tacgccgcta ctgagcttga agatctcgag    1860
atcgttgaca acaagcacaa gggcaagaag attggtcagg tcaagtcctc tggtaatctc    1920
accttcatgc gcctatttgg cggtggccac atggttccct atgaccagcc cgaggccagt    1980
ctcgagttct tcaaccgctg gatcggtggt gagtggactc agtaa                    2025

<210> SEQ ID NO 59
<211> LENGTH: 1657
<212> TYPE: DNA
<213> ORGANISM: Talaromyces cellulolyticus

<400> SEQUENCE: 59
atgtcgctac gcagctgcgc cctgctgggt ctagctgcca gcgcccttgc cgctgagccc      60
aaggtgctgc acatgccaat ggcccgcaac ccaaatgcca ccctctcgc caaacgagac     120 tctgcctccg tcaccgtcac aaatgccctg agcgagggta tctactttgt gaacgctaca    180
gttggaacac ccggtcagct ggtgcagttg gtcttggata ctggaagcag tgatgtgtgg    240
ttcttcggtc cgaattcgtg cgacgcgaaa acctctgatt gtctgggtgg aacatgtatg    300
ttttctcctt attctcctta cattccgatg ccatgtggtt ggcacgtgga tgtgcaaatc    360
gtttctgtac taatagttga taatagatga ccctcccaa tcttcgagcg tcttaatctc    420
ccaacctaaa ggccaatttt tcattcaata cggcacaccc ggctcgaatg tcactggtaa    480
ctacatcaaa gacgctttca gcgttggcga agccaaagtc acaaacctca ccatggctta    540
tgctacctac gcggcatacg ttcctaccgg tgtgatgggt attggattcg acaccaacga    600
ggccatcaca gcatatggtg gcaagcccta cccgaatttc gtcgatgttc tcaagtcgga    660
gaacgtcatt agcaccaagg catacagtct gtggttgaac gatctcgagt caagcaccgg    720
aagctgtttg tttggtggat acgataccaa gaaattctcc ggcaacctct ggctgtgcc    780 cattcaaccc gacgagtcgt ctggtgaatt gaccagtatg actgtcgcat ggactgcgct    840
tggtattacg acccaatctg gatcgcaaac aatcacttcc tcgtccttca gtcgcctgc    900 gttgctcgac tccggtacca cattgagtat catacctgat gatatctatg aatcattagt    960
cacgttcttc gatgccacac tagaccaagc aggtgatgca attgtcaaat gcaacctact   1020
cgatgactcg ggcactcttg actttacatt tggcggatcc gacggtccag ttatcaaggt   1080
```

```
tcctttctcg gagtttgcgc tacctgcaac taccaccaac ggccagcagg ccaccttcaa      1140
cgatggctcg ttggcttgtt atcttggtct tcaaggaaca ggctcggacc cgacatcaca      1200
ggtccccgtc attctcggcg acactttcct tcgctctgcc tatgttgtgt acgatctcga      1260
caacaagcaa atctctctcg cgcaaaccgt cttcaacgcg acagacagca acgtcgttga      1320
aattacgtct gccagccctg ttgccagtgt cgtgagtggc gtcacagtca cccagactgc      1380
ctctggcaac cccaacgagc tcggtgggcc tactgctact gccgacccga ccggttcagg      1440
cagctcgatc ggttcaggca gttcaggcgg ttctgatctt tccggcagca gcctcaccgt      1500
ctctcttacc cctgccacgg caaccggctc tgcatcgtca tcaacttctt ctcacaaatc      1560
gtcggctaac cccgctcctg ggccagactt tatgagcact gcccttattg ctggagcgtc      1620
tatgttgctg ggaggtgttt tcttcgtcct tcattag                               1657

<210> SEQ ID NO 60
<211> LENGTH: 1053
<212> TYPE: DNA
<213> ORGANISM: Talaromyces cellulolyticus

<400> SEQUENCE: 60
atgtgtcaat tcatttccca ttatatactt caaaaagttg ctgagtcacc tgaagtgtct        60
cagcatgcac gagaatcagc agcgaggacg ctgagtatcg acacagaggt acgaaataga       120
aggcccgatc tgcatgctgc aatcgttcag aatcccaacc tcggcaactt gcagtcagtg       180
actgcaagct cgggccgcga caaccaagt atctcagtgt acgactgtag aaacagctcc        240
aaacttccag gagtccgggt ccgaagcgat gaccagagag tcagagatcg agtcgtcaat       300
aatgcatttg acggcttaca gattgcagac aagttttata gcgatgtttt cgcatacaaa       360
gtccctgatg gttcatggaa tgctcttact ggctcagttc attttcgcga gaactacaac       420
aatgctatgt gggatggaca gcagatgatt tttggtgacg agacggaga attttcgat        480 tactttgctg attcactaga cgtaatcgtc cacgaaatta cccatggagt tacccaatac       540
acagcaaatc tgcagtacga aggccaaagc ggagcgttga atgaatctat atcagatgtt       600
tttgcatgta tggccgagca atggtatctt gaccagacag ctgaggatgg ggattggttg       660
ttaggccaaa atctgttccc tgttgcacga aagggatccg cgctgcgttc actaaagaag       720
cccggcacag cttacaacaa tgacaaaatc ctcggcaaag atccccaacc tggccatatg       780
cgtgattata caacacacg tgacgacaac ggtggtgtac atctcaattc cggcatccca       840
aatcatgcat tttatctcgt tgccactact cttggagggc gttcgtggga tcaagccggt       900
catatatggt tcaaaacttt gaccgactcc cggctcaggc ctacagctac tttcagtgcc       960
tttgctggat tgactgtgga taatgcacag agacttacg gtaacaatgt gggtcaagca      1020
gtaaagaaag cgtgggaagg ggttggtgtc tga                                  1053

<210> SEQ ID NO 61
<211> LENGTH: 40
<212> TYPE: DNA
<213> ORGANISM: Artificial Sequence
<220> FEATURE:
<223> OTHER INFORMATION: primer

<400> SEQUENCE: 61
cggtacccgg ggatcagcaa ccccaccgta atctcaaggt                              40

<210> SEQ ID NO 62
<211> LENGTH: 40
```

```
<212> TYPE: DNA
<213> ORGANISM: Artificial Sequence
<220> FEATURE:
<223> OTHER INFORMATION: primer

<400> SEQUENCE: 62
ccgatctgaa ttgacattcg gatggacttt ttgaaggcca                    40

<210> SEQ ID NO 63
<211> LENGTH: 40
<212> TYPE: DNA
<213> ORGANISM: Artificial Sequence
<220> FEATURE:
<223> OTHER INFORMATION: primer

<400> SEQUENCE: 63
tcggcgttca cttatgaggt tgacttgata gtcgatcgct                    40

<210> SEQ ID NO 64
<211> LENGTH: 40
<212> TYPE: DNA
<213> ORGANISM: Artificial Sequence
<220> FEATURE:
<223> OTHER INFORMATION: primer

<400> SEQUENCE: 64
cgactctaga ggatcgttat tgctgttgct gttgtggttg                    40

<210> SEQ ID NO 65
<211> LENGTH: 40
<212> TYPE: DNA
<213> ORGANISM: Artificial Sequence
<220> FEATURE:
<223> OTHER INFORMATION: primer

<400> SEQUENCE: 65
ccgatctgaa ttgacagata gcgtgagcac actgagcagg                    40

<210> SEQ ID NO 66
<211> LENGTH: 40
<212> TYPE: DNA
<213> ORGANISM: Artificial Sequence
<220> FEATURE:
<223> OTHER INFORMATION: primer

<400> SEQUENCE: 66
tcggcgttca cttatcaaca cgctacctct tccacagtag                    40

<210> SEQ ID NO 67
<211> LENGTH: 40
<212> TYPE: DNA
<213> ORGANISM: Artificial Sequence
<220> FEATURE:
<223> OTHER INFORMATION: primer

<400> SEQUENCE: 67
cggtacccgg ggatccgtct gtcaaggttg ggttaatcgt                    40

<210> SEQ ID NO 68
<211> LENGTH: 40
<212> TYPE: DNA
<213> ORGANISM: Artificial Sequence
<220> FEATURE:
<223> OTHER INFORMATION: primer

<400> SEQUENCE: 68
```
ccgatctgaa ttgaccgagg cagccaacca taagaactgc          40

<210> SEQ ID NO 69
<211> LENGTH: 40
<212> TYPE: DNA
<213> ORGANISM: Artificial Sequence
<220> FEATURE:
<223> OTHER INFORMATION: primer

<400> SEQUENCE: 69
tcggcgttca cttatgcgag ccgtacttgg tttgactact          40

<210> SEQ ID NO 70
<211> LENGTH: 40
<212> TYPE: DNA
<213> ORGANISM: Artificial Sequence
<220> FEATURE:
<223> OTHER INFORMATION: primer

<400> SEQUENCE: 70
cgactctaga ggatcaattg catttcttcc ccatcgtcga          40

<210> SEQ ID NO 71
<211> LENGTH: 40
<212> TYPE: DNA
<213> ORGANISM: Artificial Sequence
<220> FEATURE:
<223> OTHER INFORMATION: primer

<400> SEQUENCE: 71
cggtacccgg ggatccatag cctcatgacc aatgaccggt          40

<210> SEQ ID NO 72
<211> LENGTH: 40
<212> TYPE: DNA
<213> ORGANISM: Artificial Sequence
<220> FEATURE:
<223> OTHER INFORMATION: primer

<400> SEQUENCE: 72
ccgatctgaa ttgacgtcga tgaagtcgtc gggggtatgt          40

<210> SEQ ID NO 73
<211> LENGTH: 40
<212> TYPE: DNA
<213> ORGANISM: Artificial Sequence
<220> FEATURE:
<223> OTHER INFORMATION: primer

<400> SEQUENCE: 73
tcggcgttca cttatcggct caatatgcaa taggtgttcc          40

<210> SEQ ID NO 74
<211> LENGTH: 40
<212> TYPE: DNA
<213> ORGANISM: Artificial Sequence
<220> FEATURE:
<223> OTHER INFORMATION: primer

<400> SEQUENCE: 74
cgactctaga ggatctaggg ctaaccagca gggtaccgcc          40

<210> SEQ ID NO 75
<211> LENGTH: 40
<212> TYPE: DNA
<213> ORGANISM: Artificial Sequence

```
<220> FEATURE:
<223> OTHER INFORMATION: primer

<400> SEQUENCE: 75
cggtacccgg ggatcccaca ttcacagaag gcactataca                    40

<210> SEQ ID NO 76
<211> LENGTH: 40
<212> TYPE: DNA
<213> ORGANISM: Artificial Sequence
<220> FEATURE:
<223> OTHER INFORMATION: primer

<400> SEQUENCE: 76
ccgatctgaa ttgaccatca acatctacaa tccgacggtg                    40

<210> SEQ ID NO 77
<211> LENGTH: 40
<212> TYPE: DNA
<213> ORGANISM: Artificial Sequence
<220> FEATURE:
<223> OTHER INFORMATION: primer

<400> SEQUENCE: 77
tcggcgttca cttatgttgt tggccagaag aaagcataca                    40

<210> SEQ ID NO 78
<211> LENGTH: 40
<212> TYPE: DNA
<213> ORGANISM: Artificial Sequence
<220> FEATURE:
<223> OTHER INFORMATION: primer

<400> SEQUENCE: 78
cgactctaga ggatcctctc ccgaggcaca acccaaagtg                    40

<210> SEQ ID NO 79
<211> LENGTH: 25
<212> TYPE: DNA
<213> ORGANISM: Artificial Sequence
<220> FEATURE:
<223> OTHER INFORMATION: primer

<400> SEQUENCE: 79
gtcaattcag atcggctgcc gcctg                                    25

<210> SEQ ID NO 80
<211> LENGTH: 25
<212> TYPE: DNA
<213> ORGANISM: Artificial Sequence
<220> FEATURE:
<223> OTHER INFORMATION: primer

<400> SEQUENCE: 80
ataagtgaac gccgagtcag tacta                                    25
```